(12) United States Patent
Zhan et al.

(10) Patent No.: US 9,879,240 B2
(45) Date of Patent: Jan. 30, 2018

(54) HIGH ACTIVITY MUTANTS OF COCAINE ESTERASE FOR COCAINE HYDROLYSIS

(71) Applicant: University of Kentucky Research Foundation, Lexington, KY (US)

(72) Inventors: Chang-Guo Zhan, Lexington, KY (US); Fang Zheng, Lexington, KY (US); Lei Fang, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 173 days.

(21) Appl. No.: 14/924,181

(22) Filed: Oct. 27, 2015

(65) Prior Publication Data
US 2016/0122732 A1 May 5, 2016

Related U.S. Application Data

(60) Provisional application No. 62/073,562, filed on Oct. 31, 2014.

(51) Int. Cl.
| | |
|---|---|
| *A61K 38/00* | (2006.01) |
| *C12N 9/18* | (2006.01) |
| *A61K 38/46* | (2006.01) |

(52) U.S. Cl.
CPC .............. *C12N 9/18* (2013.01); *A61K 38/465* (2013.01); *C12Y 301/01084* (2013.01)

(58) Field of Classification Search
CPC ........ A61K 38/00; A61K 38/465; C12N 9/18; C12Y 301/01084
See application file for complete search history.

(56) References Cited

PUBLICATIONS

Carrera, M. R. A., Kaufmann, G. F., Mee, J. M., Meijler, M. M., Koob, G. F., and Janda, K. D. (2004) Treating cocaine addiction with viruses. Proc. Natl. Acad. Sci. U.S.A. 101, 10416-10421.
Meijler, M. M., Kaufmann, G. F., Q, L., Mee, J. M., Coyle, A. R., Moss, J. A., Wirsching, P., Matsushita, M., and Janda, K. D. (2005) Fluorescent cocaine probes: A tool for the selection and engineering of therapeutic antibodies. J. Am. Chem. Soc. 127, 2477-2484.
Larsen, N. A., Turner, J. M., Stevens, J., Rosser, S. J., Basran, A., Lerner, R. A., Bruce, N. C., and Wilson, I. A. (2002) Crystal structure of a bacterial cocaine esterase. Nat. Struct. Mol. Biol. 9, 17-21.
Ko, M.-C., Bowen, L .D., Narasimhan, D., Berlin, A. A., Lukacs, N. W., Sunahara, R K., Cooper, Z. D., and Woods, J. H. (2007) Cocaine esterase: Interactions with cocaine and immune responses in mice. J. Pharmacol. Exp. Ther. 320, 326-933.
Gao, D., Narasimhan, D. L., Macdonald, J., Ko, M.-C., Landry, D. W., Woods, J. H., Sunahara, R. K., and Zhan, C.-G. (2009) Thermostable variants of cocaine esterase for long-time protection against cocaine toxicity. Mol. Pharmacol. 75, 318-323.
Shoichet, B. K., Baase, W. A., Kurold, R, and Matthews, B. W. (1995) A relationship between protein stability and protein function. Proc. Natl. Acad. Sci. U.S.A. 92, 452-456.
Beadle, B. M., and Shoichet, B. K. (2002) Structural bases of stability—function tradeoffs in enzymes. J. Mol. Biol. 321, 285-296.
Tokuriki, N., Stricher, F., Serrano, L., and Tawrik, D. S. (2008) How protein stability and new functions trade off PLoS Comput. Biol. 4, e1000002.
Thomas, V. L., McReynolds, A. C., and Shoichetb, B. K. (2010) Structural bases for stability-function tradeoffs in antibiotic resistance. J. Mol. Biol. 396, 47-59.
Brim, R. L., Nance, M. R, Youngstrom, D. W., Narasimhan, D., Zhan, C.-G., Tesmer, J. J., Sunahara, R. K., and Woods, J. H. (2010) A thermally stable form of bacterial cocaine esterase: A potential therapeutic agent for treatment of cocaine abuse. Mol. Pharmacol. 77, 593-600.
Collins, G. T., Brim, R. L., Narasimhan, D., Ko, M.-C., Sunahara, R. K., Zhan, C.-G., and Woods, J. H. (2009) Cocaine esterase prevents cocaine-induced toxicity and the ongoing intravenous self-administration of cocaine in rats. J. Pharmacol. Exp. They. 331, 445-455.
Narasimhan, D., Nance, M. R., Gao, D., Ko, M.-C., Macdonald, J., Tamburi, P., Yoon, D., Landry, D. M., Woods, J. H., Zhan, C.-G., Tesmer, J. J. G., and Sunahara, R K. (2010) Structural analysis of thermostabilizing mutations of cocaine esterase. Protein. Eng. Des. Sel. 23, 537-547.
Narasimhan, D., Collins, G. T., Nance, M. R., Nichols, J., Edwald, E., Chan, J., Ko, M.-C., Woods, J. H., Tesmer, J. J. G., and Sunahara, R. K. (2011) Subunit stabilization and polyethylene glycolation of cocaine esterase improves in vivo residence time. Mol. Pharmacal. 80, 1056-1065.
Collins, G. T., Zaks, M. E., Cunningham, A. R., St, Clair, C., Nichols, J., Narasimhan, D., Ko, M.-C., Sunahara, R. K., and Woods, J. H. (2011) Effects of a long-acting mutant bacterial cocaine esterase on acute cocaine toxicity in rats. Drug Alcohol Depend. 118, 158-165.
Collins, G. T., Narasimhan, D., Cunningham, A. R., Zaks, M. E., Nichols, J., Ko, M.-C., Sunahara, R. K., and Woods, J. H. (2012) Longlasting effects of a PEGylated mutant cocaine esterase (CocE) on the reinforcing and discriminative stimulus effects of cocaine in rats. Neuropsychopharmacology 37, 1092-1103.
Collins, G. T., Brim, II L., Noon, K. R., Narasimhan, D., Lukacs, N. W., Sunahara, R. K., Woods, J. H., and Ko, M.-C. (2012) Repeated administration of a mutant cocaine esterase: Effects on plasma cocaine levels, cocaine-induced cardiovascular activity, and immune responses in rhesus monkeys. J. Pharmacol. Exp. Ther. 342, 205-213.
Yang, W., Pan, Y., Zheng, F., Cho, H., Tai, H.-H., and Zhan, C.G. (2009) Free-energy perturbation simulation on transition states and redesign of butyrylcholinesterase. Biophys. J. 96, 1931-1938.

(Continued)

*Primary Examiner* — Kagnew H Gebreyesus
(74) *Attorney, Agent, or Firm* — Stites & Harbison, PLLC; Mandy Wilson Decker

(57) ABSTRACT

The Bacterial cocaine esterase (CocE) mutants disclosed herein each have enhanced catalytic efficiency for (–)-cocaine, as compared to CocE mutants in the prior art, including CocE mutant E172-173. The presently-disclosed subject matter further includes a pharmaceutical composition including a mutant of bacterial cocaine hydrolase, as described herein, and a suitable pharmaceutical carrier. The presently-disclosed subject matter further includes a method of treating a cocaine-induced condition comprising administering to an individual an effective amount of a mutant of bacterial cocaine hydrolase variant, as disclosed herein, to accelerate cocaine metabolism and produce biologically inactive metabolites.

14 Claims, 5 Drawing Sheets

(56) References Cited

PUBLICATIONS

Hou, S., Xue, L, Yang, W., Fang, L., Zheng, F., and Zhan, C.-G. (2013) Substrate selectivity of high-activity mutants of human butyrylcholinesterase. Org. BiotnoL Chem. 11, 7477-7485.

Pan, Y., Gao, D., Yang, W., Cho, H., Yang, G., Tai, H.-H., and Zhan, C.-G. (2005) Computational redesign of human butyrylcholinesterase for anticocaine medication. Proc. Natl. Acad. Sci. U.S.A. 102, 16656-16661.

Zheng, F., Yang, W., Xue, L., Hou, S., Liu, J., and Zhan, C.-G. (2010) Design of high-activity mutants of human butyrylcholinesterase against (--)-cocaine: structural and energetic factors affecting the catalytic efficiency. Biochemistry 49, 9113-9119.

Gao, D., and Zhan, C.-G. (2006) Modeling evolution of hydrogen bonding and stabilization of transition states in the process of cocaine hydrolysis catalyzed by human butyrylcholinesterase. Proteins 62, 99-110.

Hamza, A, Cho, H., Tai, H. H., and Zhan, C.-G. (2005) Molecular dynamics simulation of cocaine binding with human butyrylcholinesterase and its mutants. J. Phys. Chem. B 109, 4776-4782.

Pan, Y., Gao, D., Yang, W., Cho, H., and Zhan, C.-G. (2007) Free energy perturbation (FEP) simulation on the transition states of cocaine hydrolysis catalyzed by human butyrylcholinesterase and its mutants. J. Am. Chem. Soc. 129, 13537-13543.

Zheng, F., Yang, W., Ko, M.-C., Liu, J., Cho, H., Gao, D., Tong, M., Tai, H.-H., Woods, J. H., and Zhan, C.-G. (2008) Most efficient cocaine hydrolase designed by virtual screening of transition states. J. Am. Chem. Soc. 130, 12148-12155.

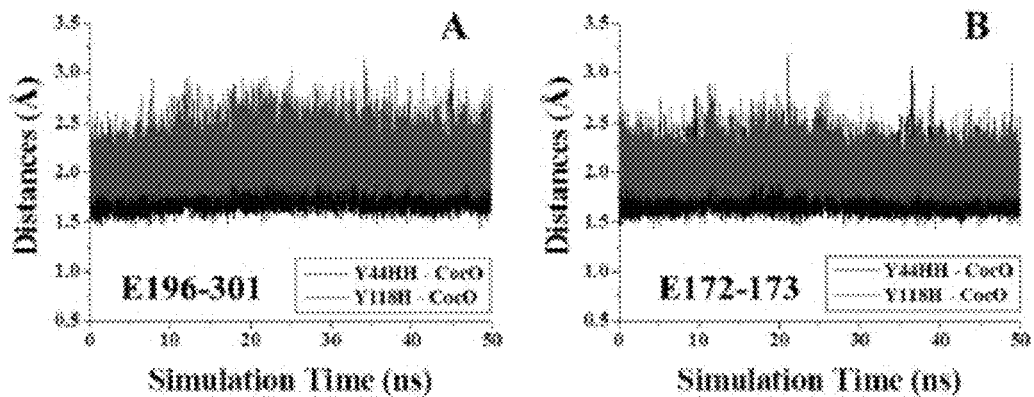
FIGS. 7A-B
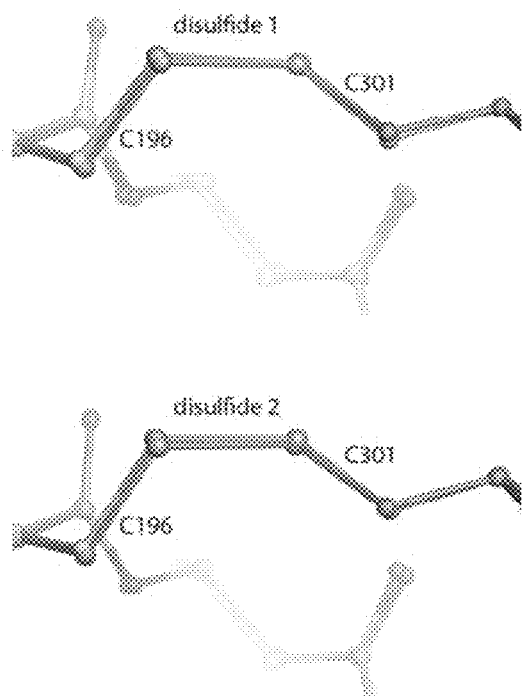
FIG. 8

SEQUENCE LISTING

<160> NUMBER OF SEQ ID NOS: 4

<210> SEQ ID NO 1
<211> LENGTH: 1722
<212> TYPE: DNA
<213> ORGANISM: Rhodococcus sp. MB1

<400> SEQUENCE: 1
atggtggacg ggaattacag tgttgcctcg aacgtgatgg ttccgatgcg tgatggggtg     60
cgtctggcgg tcgacctgta ccgaccagat gctgatggac ctgttccggt cctgctggtt    120
cgcaacccat acgacaagtt cgacgtgttc gcgtggtcga cgcagtcgac aaactggctt    180
gagttcgtgc gtgatggcta tgccgtggtc attcaagaca cgcgtggctt gttcgcatcg    240
gaaggtgagt tcgtcccgca cgttgacgac gaagctgacg ccgaggatac gttgagctgg    300
attctggaac aagcgtggtg cgacggcaat gtgggcatgt tcggcgtttc gtacttgggt    360
gtgacccagt ggcaggccgc cgtatccggc gttggtgggc tgaaggcgat cgcgccgtcc    420
atggcgtcgg cggacttgta ccgcgccccg tggtacggcc ctggtggtgc gctttcagtc    480
gaggcgctgt tgggctggtc agctctcata ggtactgggc tcatcacgtc gaggtctgac    540
gcccggccgg aagacgcagc cgacttcgtc caactcgcag caattctcaa tgacgtcgct    600
ggcgcggcgt cggtcacgcc cctggccgag caaccgcttc tgggccgact gattccgtgg    660
gtgatcgatc aggttgtcga tcaccccgac aacgatgaat catggcagtc cattagcttg    720

```
tttgaacgac tcggcgggtt ggcaacaccg gccttgatca cggctgggtg gtacgacggg    780
ttcgtcggcg aatcgttgcg cactttcgtt gcggtcaagg acaatgccga cgcacgtttg    840
gttgtcggcc cttggagtca cagcaacctc actggtcgga atgcggaccg gaagttcggc    900
attgccgcga cctacccgat tcaagaagcc accacgatgc acaaggcatt cttcgaccgg    960
cacctccgcg gcgagaccga tgcactcgca ggcgtcccca agtgcggct gttcgtaatg   1020
ggcatcgatg agtggcgtga cgaaacggac tggccactgc cggacacggc gtatacgccc   1080
ttctatcttg gaggtagcgg ggctgcgaat acctccacgg gtggtggaac actgtcgacg   1140
tcgatttccg gaactgaatc tgctgacacc tacctgtatg atccggccga tcccgtgcct   1200
tcgctcgggg gacgctgct gttccacaac ggagacaacg acccgccga ccaacgtccc   1260
attcatgacc gggacgacgt gttgtgttac agcactgagg tattgaccga cccggtggaa   1320
gtaaccggca ccgtctccgc ccggctgttc gtgtcgtcat cagcggtgga cactgatttc   1380
accgccaaac ttgtcgacgt atttcccgac ggtcgcgcga tcgcgctgtg tgacgggatc   1440
gtgcggatgc ggtaccgcga acgttggtc aatccaacct tgatcgaagc gggcgaaatc   1500
tacgaggttg ctatcgacat gcttgcaacc tcgaatgtat tcctgccagg gcatcgcatc   1560
atggtccaag tatcaagtag caacttcccg aaatacgacc gcaattcgaa taccggcgga   1620
gtaatcgcac gggaacagct cgaagagatg tgcaccgccg tgaaccgcat tcaccgagga   1680
cctgagcatc ccagccacat tgtgctgccg attatcaagc ga                      1722

<210> SEQ ID NO 2
<211> LENGTH: 574
<212> TYPE: PRT
<213> ORGANISM: Rhodococcus sp. MB1

<400> SEQUENCE: 2

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
        50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190
```

-continued

```
Ala Ala Ile Leu Asn Asp Val Ala Gly Ala Ala Ser Val Thr Pro Leu
            195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
                260                 265                 270

Lys Asp Asn Ala Asp Ala Arg Leu Val Val Gly Pro Trp Ser His Ser
            275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
                340                 345                 350

Leu Pro Asp Thr Ala Tyr Thr Pro Phe Tyr Leu Gly Gly Ser Gly Ala
            355                 360                 365

Ala Asn Thr Ser Thr Gly Gly Thr Leu Ser Thr Ser Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
                435                 440                 445

Leu Phe Val Ser Ser Ser Ala Val Asp Thr Asp Phe Thr Ala Lys Leu
450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
            515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570
```

<210> SEQ ID NO 3
<211> LENGTH: 1722
<212> TYPE: DNA
<213> ORGANISM: Artificial Sequence
<220> FEATURE:
<223> OTHER INFORMATION: Synthesized

<400> SEQUENCE: 3

```
atggtggacg ggaattacag tgttgcctcg aacgtgatgg ttccgatgcg tgatggggtg      60
cgtctggcgg tcgacctgta ccgaccagat gctgatggac ctgttccggt cctgctggtt     120
cgcaacccat acgacaagtt cgacgtgttc gcgtggtcga cgcagtcgac aaactggctt     180
gagttcgtgc gtgatggcta tgccgtggtc attcaagaca cgcgtggctt gttcgcatcg     240
gaaggtgagt tcgtcccgca cgttgacgac gaagctgacg ccgaggatac gttgagctgg     300
attctggaac aagcgtggtg cgacggcaat gtgggcatgt tcggcgtttc gtacttgggt     360
gtgacccagt ggcaggccgc cgtatccggc gttggtgggc tgaaggcgat cgcgccgtcc     420
atggcgtcgg cggacttgta ccgcgccccg tggtacggcc tggtggtgc gctttcagtc     480
gaggcgctgt tgggctggtc agctctcata ggtcgccagc tcatcacgtc gaggtctgac     540
gcccggcccg aagacgcagc cgacttcgtc caactcgcag caatttgcaa tgacgtcgct     600
ggcgcggcgt cggtcacgcc cctggccgag caaccgcttc tgggccgact gattccgtgg     660
gtgatcgatc aggttgtcga tcaccccgac aacgatgaat catggcagtc cattagcttg     720
tttgaacgac tcggcgggtt ggcaacaccg gccttgatca cggctgggtg gtacgacggg     780
ttcgtcggcg aatcgttgcg cactttcgtt gcggtcaagg acaatgccga cgcacgtttg     840
gttgtcggcc cttggagtca cagcaacctc actggtcgga atgcggaccg gaagttcggc     900
tgcgccgcga cctacccgat tcaagaagcc accacgatgc acaaggcatt cttcgaccgg     960
cacctccgcg gcgagaccga tgcactcgca ggcgtcccca agtgcggct gttcgtaatg    1020
ggcatcgatg agtggcgtga cgaaacggac tggccactgc cggacacggc gtatacgccc    1080
ttctatcttg gaggtagcgg ggctgcgaat acctccacgg tggtggaac actgtcgacg    1140
tcgatttccg gaactgaatc tgctgacacc tacctgtatg atccggccga tcccgtgcct    1200
tcgctcgggg ggacgctgct gttccacaac ggagacaacg acccgccga ccaacgtccc    1260
attcatgacc gggacgacgt gttgtgttac agcactgagg tattgaccga cccggtggaa    1320
gtaaccggca ccgtctccgc ccggctgttc gtgtcgtcat cagcggtgga cactgatttc    1380
accgccaaac ttgtcgacgt atttcccgac ggtcgcgcga tcgcgctgtg tgacgggatc    1440
gtgcggatgc ggtaccgcga acgttggtc aatccaacct tgatcgaagc gggcgaaatc    1500
tacgaggttg ctatcgacat gcttgcaacc tcgaatgtat tcctgccagg gcatcgcatc    1560
atggtccaag tatcaagtag caacttcccg aaatacgacc gcaattcgaa taccggcgga    1620
gtaatcgcac gggaacagct cgaagagatg tgcaccgccg tgaaccgcat tcaccgagga    1680
cctgagcatc ccagccacat tgtgctgccg attatcaagc ga                       1722
```

<210> SEQ ID NO 4
<211> LENGTH: 574
<212> TYPE: PRT
<213> ORGANISM: Artificial Sequence
<220> FEATURE:
<223> OTHER INFORMATION: Synthesized

<400> SEQUENCE: 4

```
Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
        35                  40                  45
```

-continued

```
Val Phe Ala Trp Ser Thr Gln Ser Thr Asn Trp Leu Glu Phe Val Arg
 50                  55                  60

Asp Gly Tyr Ala Val Val Ile Gln Asp Thr Arg Gly Leu Phe Ala Ser
 65                  70                  75                  80

Glu Gly Glu Phe Val Pro His Val Asp Asp Glu Ala Asp Ala Glu Asp
                     85                  90                  95

Thr Leu Ser Trp Ile Leu Glu Gln Ala Trp Cys Asp Gly Asn Val Gly
                100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Ala Leu Ser Val
145                 150                 155                 160

Glu Ala Leu Leu Gly Trp Ser Ala Leu Ile Gly Arg Gln Leu Ile Thr
                165                 170                 175

Ser Arg Ser Asp Ala Arg Pro Glu Asp Ala Ala Asp Phe Val Gln Leu
                180                 185                 190

Ala Ala Ile Cys Asn Asp Val Ala Gly Ala Ala Ser Val Thr Pro Leu
            195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
                260                 265                 270

Lys Asp Asn Ala Asp Ala Arg Leu Val Val Gly Pro Trp Ser His Ser
            275                 280                 285

Asn Leu Thr Gly Arg Asn Ala Asp Arg Lys Phe Gly Cys Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Gly Ser Gly Ala
                355                 360                 365

Ala Asn Thr Ser Thr Gly Gly Gly Thr Leu Ser Thr Ser Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
                435                 440                 445

Leu Phe Val Ser Ser Ser Ala Val Asp Thr Asp Phe Thr Ala Lys Leu
            450                 455                 460
```

```
Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
        530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570
```

US 9,879,240 B2

HIGH ACTIVITY MUTANTS OF COCAINE ESTERASE FOR COCAINE HYDROLYSIS

RELATED APPLICATIONS

This application claims priority from U.S. Provisional Application Ser. No. 62/073,562 filed Oct. 31, 2014, the entire disclosure of which is incorporated herein by this reference.

GOVERNMENT SUPPORT CLAUSE

This invention was made with Government support under NIH number NIH R01 DA025100. The Government has certain rights in this invention.

TECHNICAL FIELD

The presently-disclosed subject matter relates to therapeutic enzymes, such as a mutant of bacterial cocaine hydrolase, in particular, cocaine esterase (CocE) polypeptide variant(s) with amino acid substitutions relative to wild type CocE.

INTRODUCTION

Cocaine overdose and addiction have resulted in serious medical and social problems in modern society. (1) So far, there is no anticocaine medication approved by the Food and Drug Administration (FDA). (2, 3) Cocaine causes physiological effects by binding with the dopamine transporter and, thus, blocking dopamine reuptake. The disastrous medical and social consequences of cocaine abuse have made the development of an anticocaine medication a high priority. However, despite decades of efforts, the classical pharmacodynamic approach has failed to yield a truly useful small-molecule receptor/transporter antagonist. The alternative pharmacokinetic approach is to interfere with the delivery of cocaine to its receptors and/or accelerate its metabolism in the body. (2, 4-8) It would be an ideal to develop an exogenous enzyme which can accelerate cocaine metabolism and produce biologically inactive metabolites.

Bacterial cocaine esterase (CocE) has been recognized as the most efficient natural enzyme for hydrolyzing the naturally occurring (−)-cocaine. (9) No other natural esterase has a catalytic activity for cocaine comparable to that of CocE. Studies have shown that CocE can help to prevent extreme cocaine toxicity and can even prevent the lethal effects of cocaine in some subjects. (10) However, a major obstacle to the clinical application of CocE is the thermoinstability of wild-type CocE with a half-life of only about 12 minutes at physiological temperature (37° C.). (11) It is highly desirable to develop thermostable mutants of CocE for therapeutic treatment of cocaine abuse (overdose and addiction). In fact, thermal stability is a well-known common problem in protein drug development. (11) In general, the more thermally stable a protein drug, the longer shelf half-life the protein drug can have.

Generally speaking, the thermal stability of a protein can be improved by enhancing the weak interactions inside the enzyme through either noncovalent forces, such as hydrogen bonds, (12) or covalent linkage, such as disulfide bonds. (13) Particularly for an enzyme, besides improving its stability, it is also important to maintain the catalytic activity of the enzyme. However, it is much more challenging to engineer an enzyme with an improved stability without decreasing the catalytic activity. (14-16) In general, according to the commonly recognized "stability-function trade-off" theory/hypothesis, (14) protein residues that contribute to catalysis or ligand binding are not optimal for protein stability and, thus, there is a balance between the stability and function. Indeed, extensive studies (14, 17-22) demonstrate that thermostabilizing mutations of enzymes decrease the catalytic activities of those enzymes and that mutations improving the catalytic activities decrease the thermal stability. Nevertheless, some CocE mutants with an improved thermal stability have successfully been designed and discovered in recently reported studies, (11, 23-26) and these thermostable mutants do not decrease, or only slightly decrease, the catalytic efficiency ($k_{cat}/K_M$) of CocE against cocaine. Further animal behavior studies (27-29) reveal that these CocE mutants are promising in development of an enzyme therapy for cocaine abuse.

Notably, one of the reported thermostable mutants of CocE, i.e. the T172R/G173Q mutant (known as drug RBP-8000, with ClinicalTrials.gov Identifier of NCT01846481 in clinical development) designed through computational modeling and simulations (11) has been advanced to the randomized, double-blind, placebo controlled clinical trial phase II for cocaine overdose treatment. The T172R/G173Q mutant (denoted as enzyme E172-173 here for convenience) was designed through introducing favorable noncovalent forces including a hydrogen bond between domains I and II of the protein. (11) This CocE mutant has an in vitro half-life of about 6 hours at 37° C. without decreasing the catalytic activity of CocE against cocaine. (11) The half-life of about 6 hours at 37° C. is long enough for cocaine overdose treatment, because one just needs to use the enzyme to rapidly detoxify cocaine. However, for cocaine addiction treatment, it is desirable to have a highly efficient cocaine-metabolizing enzyme in the body with a residence time as long as possible. With a highly efficiently cocaine-metabolizing enzyme in the body, whenever a cocaine abuser uses cocaine again, the enzyme would rapidly metabolize cocaine so that the cocaine abuser would not feel the stimulant effects of cocaine.

To further develop an improved therapeutic enzyme for cocaine abuse treatment, one would like to both extend the half-life of E172-173 at 37° C. and improve the catalytic efficiency against cocaine. It has been shown (11, 15, 26) that the thermal stability of E172-173 at 37° C. can be enhanced by extra mutations on E172-173. However, none of the reported extra mutations on E172-173 improved the catalytic efficiency against cocaine.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Here, a rationally-designed new mutant of E172-173 is reported, which has not only considerably extended the in vitro half-life at 37° C., but also significantly improved the catalytic efficiency against cocaine. The new CocE mutant (i.e. the T172R/G173Q/L196C/I301C mutant of CocE, denoted as enzyme E196-301 for convenience) was modified further via PEGylation in order to extend the in vivo residence time of the enzyme. The PEGylated E196-301 was used to fully protect mice from a lethal dose of cocaine (180 mg/kg, $LD_{100}$) for at least 3 days, indicating that it might be a more promising enzyme candidate for development of novel anticocaine therapeutics.

Hence, the presently-disclosed subject matter includes a mutant of bacterial cocaine hydrolase. The presently-disclosed subject matter includes a new mutant of E172-173. In some instances, the mutant enzyme has one or more cross-subunit disulfide bond. In some embodiments, the one cross-subunit disulfide bond is a bond between C196a and C301b, or C301a and C196b. In some preferred embodiments, the enzyme has a pair of cross-subunit disulfide bonds at C196a and C301b, and C301a and C196b.

In some embodiments, the mutant of bacterial cocaine hydrolase provides improved stability and/or improved catalytic activity against cocaine. In some embodiments, the mutant of bacterial cocaine hydrolase provides improved stability and/or improved catalytic activity against cocaine. In some embodiments, the mutant bacterial cocaine hydrolase includes at least one polyethylene glycol polymer chain attached thereto. In some embodiments, the pegylation improves stability of the enzyme. In some preferred embodiments, the hydrolase is conjugated to a maleimide linked polyethylene glycol. In some embodiments, the PEG molecule is branched.

The presently disclosed subject matter further includes a pharmaceutical composition that includes a bacterial cocaine hydrolase variant and a suitable pharmaceutical carrier.

The presently-disclosed subject matter further includes a method of treating a cocaine-induced condition, which includes administering to an individual an effective amount of bacterial cocaine hydrolase variant or a pharmaceutical composition comprising a bacterial cocaine hydrolase variant, as described herein, to accelerate cocaine metabolism and produce biologically inactive metabolites. In some embodiments, the bacterial cocaine hydrolase variant exhibits a one-hundred-fold or more increase in cocaine hydrolysis catalytic efficiency compared to compared to E172-E73 mutant hydrolase, which is currently in clinical trials for treatment of cocaine overdose.

BRIEF DESCRIPTION OF THE DRAWINGS

The novel features of the subject matter of the present disclosure are set forth with particularity in the following description and in the appended sample claims. A better understanding of the features and advantages of the presently disclosed subject matter will be obtained by reference to the following detailed description that sets forth illustrative embodiments, in which the principles of the invention(s) are used, and the accompanying drawings.

(FIG. 1A) The time-dependent Cα-Cα distances between L196 and I301 in the MD-simulated dimer structure of E172-173. The letters a and b indicated after the residue numbers refer to subunits a and b, respectively. (FIG. 1B) The modeled E172-173 dimer structure shown in ribbons (with a and b referring to subunits a and b, respectively), domain I is shown in red, domain II is shown in green, and domain III is shown in yellow. (FIG. 1C) Key residues L196 (a/b) and I301 (a/b) shown in ball and sticks on the dimer interface.

(FIG. 2A) T172R/G173Q (FIG. 2B) T172R/G173Q/G4C/S10; (FIG. 2C) T172R/G173Q/L196C/I301C.

(FIG. 4A) Ribbons representation of the homodimeric molecule generated by applying 2-fold crystallographic symmetry. The side chains of the cysteine residues forming intersubunit disulfide bonds are shown in a space filling representation. (FIG. 4B) View of the dimer rotated 90° about a horizontal axis. (FIG. 4C) Fo-Fc electron density (green, 3.5 sigma contour) calculated with the rigidly placed (before refinement) molecular replacement model having residues 196 and 301 altered to glycines. The final refined model in a stick representation is superimposed on the map. (FIG. 4D) Final SIGMAA-weighted 2Fo-Fc electron density map (blue, 1.0 sigma cutoff) in the region of the disulfide bond with the final model shown in a stick representation.

FIGS. 7A-7B show the time-dependence of important H . . . O distances (relevant to hydrogen bonds) from the MD-simulated E172-173 and E196-301 structures. Y44HH-CocO represents the distance between the hydroxyl hydrogen (denoted as HH) of the Y44 side chain and the carbonyl oxygen (denoted as CocO) of (−)-cocaine benzoyl ester. Y118H-CocO refers to the distance between hydrogen (H) of the Y118 backbone and the carbonyl oxygen (CocO) of (−)-cocaine benzoyl ester. E172-173 refers to T172R/G173Q CocE, and E196-301 refers to T172R/G173Q/L196C/I301C CocE.

FIG. 8 is an illustration of intermonomer disulfide bonds in the CocE mutant (E196-301) dimer refined in space group P65. The complete process of structure determination was carried out in a space group with lower symmetry than the true space group (P6522) in order to assess the effects of the dimer being located on a crystallographic two-fold axis. Noncrystallographic symmetry restraints were not used during refinement. The panels show the two, now not strictly identical, disulfide bonds for the final model (Rwork—0.17, Rfree—0.21; yellow carbons) superimposed on the identical disulfide bonds in the model refined on the crystallographic two-fold axis (cyan carbons).

BRIEF DESCRIPTION OF THE SEQUENCE LISTING

Figures 1A, 1B, 1C:
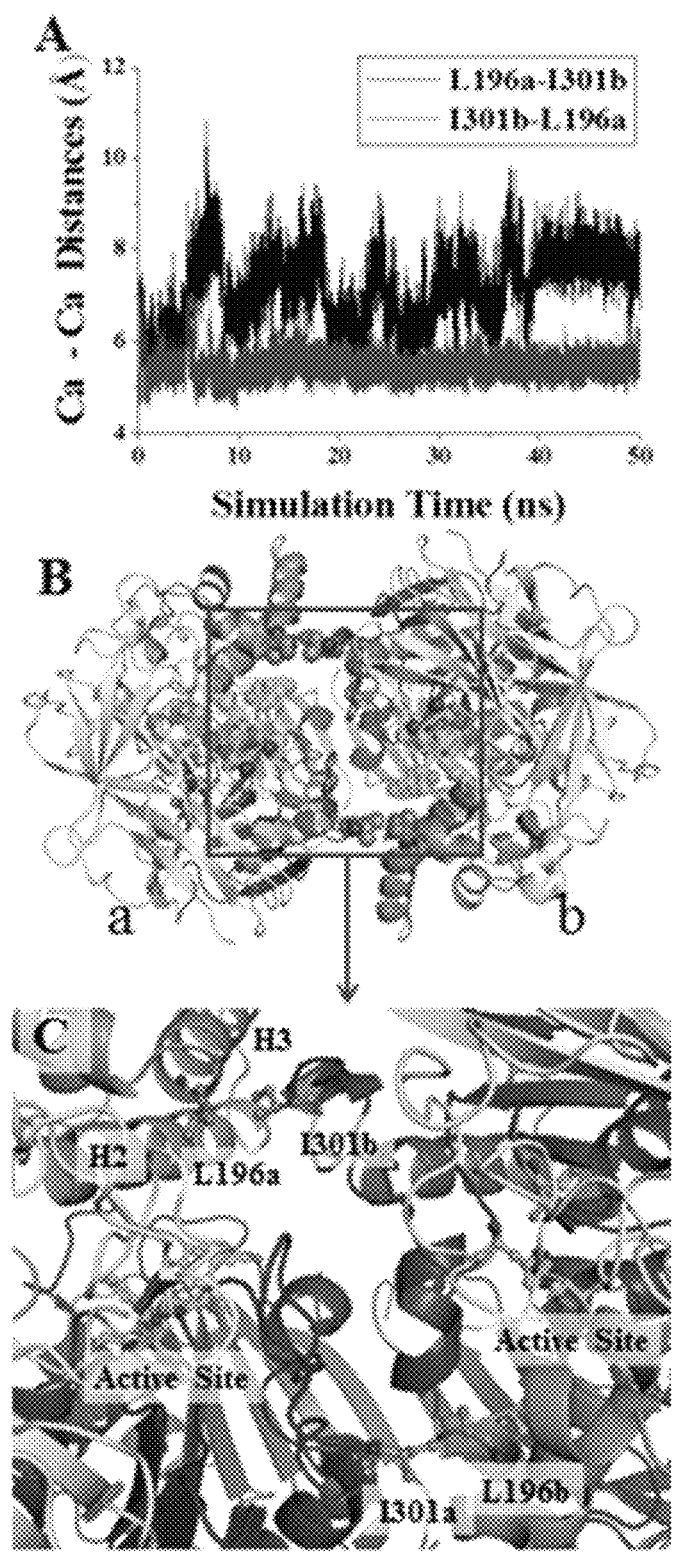
FIGS. 1A-1C present a modeled E172-173 dimer structure.

SEQ ID NO: 1 is a nucleotide sequence encoding wild type cocaine esterase (CocE) polypeptide of SEQ ID NO: 2.

SEQ ID NO: 2 is the amino acid of wild type CocE.

SEQ ID NO: 3 is a nucleotide sequence encoding the CocE polypeptide variant of SEQ ID NO: 4;

SEQ ID NO: 4 is an amino acid sequence encoding the CocE polypeptide variant having the following amino acid substitutions, as compared to wild type CocE: T172R, G173Q, L196C, and I301C.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter is illustrated by specific but non-limiting examples throughout this description. The examples may include compilations of data that are representative of data gathered at various times during the course of development and experimentation related to the present invention(s). Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The presently-disclosed subject matter includes cocaine hydrolase (CocE) polypeptide variants. In some embodiments, the CocE polypeptide variant is a mutant of E172-173. The CocE polypeptide variants disclosed herein each have enhanced catalytic efficiency for (−)-cocaine, as compared to CocE mutants in the prior art, including CocE mutant E172-173.

The presently-disclosed subject matter further includes a pharmaceutical composition including a butyrylcholinesterase polypeptide variant, as described herein, and a suitable pharmaceutical carrier. The presently-disclosed subject matter further includes a method of treating a cocaine-induced condition comprising administering to an individual an effective amount of a butyrylcholinesterase polypeptide variant, as disclosed herein, to lower blood cocaine concentration.

While the following terms used herein are believed to be well understood by one of ordinary skill in the art, definitions are set forth to facilitate explanation of the presently-disclosed subject matter.

The terms "polypeptide", "protein", and "peptide", which are used interchangeably herein, refer to a polymer of the protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The term "variant" or "mutant" refers to an amino acid sequence that is different from the reference polypeptide by one or more amino acids, e.g., one or more amino acid substitutions. For example a CocE polypeptide variant differs from wild-type CocE by one or more amino acid substitutions, i.e., mutations.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus, carboxy-terminus of the reference polypeptide, or alternatively both. For example, CocE polypeptide fragment can have 1, 2, 3, 4, 5, 6, 7, 8, 9, or 10 fewer amino acids than a full-length wild-type CocE polypeptide. CocE polypeptide fragments are also inclusive of fragments of CocE polypeptide variants.

The term "cocaine" may refer to any and all forms of cocaine, including smoked, heated, inhaled, or injected cocaine. Further, in some embodiments, the term "cocaine" refers to any substance obtained, isolated and/or derived from the leaves of a coca plant. And in certain embodiments, the term "(−)-cocaine" refers to methyl (1R,2R,3S,5S)-3-(benzoyloxy)-8-methyl-8-azabicyclo[3.2.1]octane-2-carboxylate.

Unless otherwise indicated, the term "administering" is inclusive of all means known to those of ordinary skill in the art for providing a preparation to a subject, including administration by inhalation, nasal administration, topical administration, intravaginal administration, ophthalmic administration, intraaural administration, intracerebral administration, intravitreous administration, intracameral administration, posterior sub-Tenon administration, posterior juxtascleral administration, subretinal administration, suprachoroidal administration, cell-based administration or production, rectal administration, and parenteral administration, including injectable such as intravenous administration, intra-arterial administration, intramuscular administration, and/or subcutaneous administration. Administration can be continuous or intermittent. A preparation can be administered therapeutically; that is, administered to treat an existing condition of interest. A preparation can be administered prophylactically; that is, administered for prevention of a condition of interest.

In some embodiments a subject will be administered an effective amount of at least one enzyme, compound and/or composition provided in the present disclosure. In this respect, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Additionally, the terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "subject" includes human and veterinary subjects.

In some embodiments the subject in need thereof will be suffering or will have been diagnosed cocaine addiction and/or related diseases, disorders, pathologies, or conditions.

As used herein, the terms "treatment" or "treating" relate to any treatment of a condition of interest, including but not limited to prophylactic treatment and therapeutic treatment. As such, the terms treatment or treating include, but are not limited to: preventing a condition of interest or the development of a condition of interest; inhibiting the progression of a condition of interest; arresting or preventing the development of a condition of interest; reducing the severity of a condition of interest; ameliorating or relieving symptoms associated with a condition of interest; and causing a regression of the condition of interest or one or more of the symptoms associated with the condition of interest.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "an enzyme" includes a plurality of such enzymes, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As will be recognized by one of ordinary skill in the art, the terms "reduce", "reducer", "reduction", "reducing", "suppression," "suppressing," "suppressor," "inhibition," "inhibiting" or "inhibitor" do not refer to a complete elimination of angiogenesis in all cases. Rather, the skilled artisan will understand that the term "reducing", "suppressing" or "inhibiting" refers to a reduction or decrease in a particular condition. Such reduction or decrease can be determined relative to a control. In some embodiments, the reduction or decrease relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

As described herein, the presently-disclosed subject matter further includes pharmaceutical compositions comprising at least one enzyme described herein together with a pharmaceutically acceptable carrier.

The term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound. For buccal administration the compositions can take the form of tablets or lozenges formulated in conventional manner.

The compositions can be formulated as eye drops. For example, the pharmaceutically acceptable carrier may comprise saline solution or other substances used to formulate eye drop, optionally with other agents. Thus, eye drop formulations permit for topical administration directly to the eye of a subject.

The compositions can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds can also be formulated in rectal compositions, creams or lotions, or transdermal patches.

The presently-disclosed subject matter further includes a kit that can include an enzyme and/or a pharmaceutical composition as described herein, packaged together with a device useful for administration of the compound or composition. As will be recognized by those or ordinary skill in the art, the appropriate administration-aiding device will depend on the formulation of the compound or composition that is selected and/or the desired administration site. For example, if the formulation of the compound or composition is appropriate for injection in a subject, the device could be a syringe. For another example, if the desired administration site is cell culture media, the device could be a sterile pipette.

The presently-disclosed subject matter includes mutants of bacterial cocaine hydrolase. The CocE polypeptide variants disclosed herein each have enhanced catalytic efficiency for (−)-cocaine, as compared to CocE variant presently in trials. The presently-disclosed subject matter further includes a pharmaceutical composition including a bacterial cocaine hydrolase mutant, as described herein, and a suitable pharmaceutical carrier. The presently-disclosed subject matter further includes a method of treating a cocaine-induced condition comprising administering to an individual an effective amount of a bacterial cocaine hydrolase mutant, as disclosed herein, to accelerate cocaine metabolism and produce biologically inactive metabolites.

In some embodiments, the present disclosure provides a CocE polypeptide variant for treatment of cocaine abuse. Moreover, the CocE polypeptide variant(s) of the present disclosure may have (i) an improved in vitro and/or in vivo half-life and/or (ii) an improved catalytic activity and/or catalytic efficiency, as compared to therapeutic enzymes previously known in the art.

Some embodiments of the present disclosure provide a mutant of bacterial cocaine hydrolase. And in some embodiments, the mutant of bacterial cocaine hydrolase provides improved stability and/or improved catalytic activity against cocaine.

In certain embodiments, the CocE polypeptide variant of the present disclosure comprises a T172R/G173Q mutant. In some embodiments, the enzyme of the present disclosure comprises a T172R/G173Q/L196C/1301C mutant of cocaine esterase (CocE). In a particular embodiment, the CocE polypeptide variant of the present disclosure comprises E172-173 enzyme. And in some embodiments, the CocE polypeptide variant(s) of the present disclosure comprises E196-301. Furthermore, in some embodiments, the enzyme(s) of the present disclosure may be modified by PEGylation. And in certain embodiments, treatment and/or modification of an enzyme via PEGylation extends the in vivo residence time of the enzyme.

Numerous derivatives of PEG and methods for making them and conjugating them to an enzyme are known in the art and are suitable for use in the present invention. In some preferred embodiments, the PEG contains maleimide which reacts selectively with thiol residues in a Michael addition reaction. Other functionalized PEGs can be used in embodiments, and adjusted according to desired properties of the PEGylated enzyme, for example in vivo residence time.

In some embodiments, the enzyme(s) of the present disclosure may have an in vitro and/or in vivo half-life of between about 1 hour and about 1 year and/or of any amount of time within that range.

Additionally, in certain embodiments, the enzyme(s) of the present disclosure may have an in vitro and/or in vivo half-life of between about 4 and about 8 hours, between about 5 and about 7 hours or between about 5.5 and about 6.5 hours. And in some embodiments, the enzyme(s) of the present disclosure have an in vitro and/or in vivo half-life of about 6 hours. Moreover, any such half-life is or can be maintained at physiological temperature in a human subject. In other words, in certain embodiments, the enzyme(s) of the present disclosure may have an in vitro and/or in vivo half-life of between about 4 and about 8 hours at a temperature at or around physiological temperature in a human subject. Thus, in some embodiments, the enzyme(s) of the present disclosure have an in vitro and/or in vivo half-life of between about 4 and about 8 hours between about 36.5° C. and about 37.5° C., which is normal human body temperature.

Meanwhile, in other embodiments, the enzyme(s) of the present disclosure may have an in vitro and/or in vivo half-life of greater than about 100 days. And in some embodiments, the enzyme(s) of the present disclosure have an in vitro and/or in vivo half-life of between about 1 and about 150 days. Moreover, any such half-life is or can be maintained at physiological temperature in a human subject. In other words, in certain embodiments, the enzyme(s) of the present disclosure may have a half-life of greater than about 100 days at a temperature at or around physiological temperature in a human subject. Thus, in some embodiments, the enzyme(s) of the present disclosure have an in vitro and/or in vivo half-life of greater than or equal to about 100 days at about 36.5° C. and about 37.5° C. and/or at a normal and/or an average human body temperature.

In certain embodiments, the present disclosure further provides a method of treating, preventing and/or reducing substance abuse, such as cocaine abuse and/or cocaine addiction. In the present disclosure, "substance abuse" may include, for example, craving, drug seeking, and/or self-administration. The method comprises at least the step of administering a CocE polypeptide variant provided in the present disclosure to a subject. In some embodiments, the subject is in need of treatment.

Cocaine esterase is known as the most efficient natural enzyme for cocaine hydrolysis. A major obstacle to the clinical application of wild-type CocE is the thermoinstability with a half-life of only about 12 minutes at 37° C. The previously designed T172R/G173Q mutant (denoted as enzyme E172-173) with an improved in vitro half-life of about 6 hours at about 37° C. is currently in clinical trial Phase II for cocaine overdose treatment.

Through molecular modeling and dynamics simulation, the inventors of the present disclosure have designed and characterized a new mutant of E172-173 with extra L196C/I301C mutations (denoted as enzyme E196-301) to produce cross-subunit disulfide bonds that stabilize the dimer structure. The cross-subunit disulfide bonds were confirmed by X-ray diffraction. The designed L196C/I301C mutations have not only considerably extended the in vitro half-life at 37° C. to >100 days, but also significantly improved the catalytic efficiency against cocaine by about 150%.

In addition, the thermostable E196-301 can be PEGylated to significantly prolong the residence time in a subject. For example, the PEGylated E196-301 can fully protect mice from a lethal dose of cocaine (180 mg/kg, LD100) for at least 3 days, with an average protection time of about 94 hours. This is the longest in vivo protection of mice from the lethal dose of cocaine demonstrated within all studies using an exogenous enzyme reported so far. Hence, E196-301 may become a valuable therapeutic enzyme for cocaine abuse treatment, and it demonstrates that a general design strategy and protocol to simultaneously improve both the stability and function are feasible for rational protein drug design.

Accordingly, in some embodiments, an enzyme of the present disclosure may be pegylated. In other words, in some embodiments, at least one chain of polyethylene glycol (PEG) polymer may be attached to the enzyme of interest. And in certain embodiments, the pegylation (process via which the enzyme is pegylated) of an enzyme may improve the enzyme's residence time in a subject.

Further, in some embodiments, the present disclosure is directed to a method of protecting a subject from an overdose and/or a lethal dose of cocaine. The method includes at least the step of administering an amount of at least one enzyme of the present disclosure to a subject. In some embodiments, administration of an effective amount of an enzyme of the present disclosure can protect a subject from and overdose and/or a lethal dose of cocaine for between about 24 and about 100 hours. In certain embodiments, administration of an effective amount of an enzyme of the present disclosure protects a subject from overdose and/or lethal dose of cocaine for at least about 48 hours, at least about 72 hours, and/or at least about 96 hours.

In some embodiments, the enzyme of the present disclosure comprises a dimer. And in certain embodiments, the enzyme of the present disclosure has been modified to include disulfide bonds between the two subunits of the dimer. Indeed, in certain embodiments, disulfide bonds are introduced between the subunits of an enzyme of the present disclosure. These disulfide bonds are referred to as cross-subunit disulfide bonds.

Additionally, in some embodiments, the enzyme of the present disclosure includes at least one mutation that increases the size of the active site cavity of the enzyme. And in certain embodiments, the at least one mutation improves the catalytic activity of the enzyme.

The presently-disclosed subject matter is illustrated by the following specific but non-limiting examples. The following examples may include compilations of data that are representative of data gathered at various times during the course of development and experimentation related to the present invention.

EXAMPLES

Mutant Design: Insights from Molecular Modeling.

The inventors of the present disclosure first aimed to stabilize the dimer structure of E172-173 and then analyzed the possibly stabilized dimer structure and estimated how the activity of the dimer would change. The computational design strategy relied on the molecular dynamics (MD)-simulated dimer structure of E172-173 and the idea that the dimer structure can be stabilized by introducing disulfide bonds between the two subunits of the dimer. So, the inventors carried out a sufficiently long MD simulation (50 ns) on the E172-173 dimer structure in order to obtain a dynamically stable dimer structure. To search for appropriate mutational sites to introduce the cross-subunit disulfide bonds, a self-developed script was used to scan the key internuclear distances between the Cα atoms of the residues on the dimer interface from the collected snapshots of the MD trajectory. Essentially, each pair of residues from different subunits was evaluated computationally for the simulated Cα-Cα distance. If the simulated Cα-Cα distance was within 7 Å, the pair of the residues would be checked manually for further evaluation of the detailed interactions. The most hopeful pair of residues may be mutated to cysteine for introducing possible cross-subunit disulfide bond(s).

Based on the analysis of the MD trajectory, L196C/I301C mutations satisfied all of the structural requirements. Summarized in Table 1 are the maximum, minimum, and average values of the Cα-Cα distances associated with the stable MD trajectory (10 to 50 ns) in comparison with the corresponding Cα-Cα distances in the X-ray crystal structure. As seen in Table 1, the detailed analysis of the MD trajectory predicted that extra L196C/I301C mutations on E172-173 may introduce the desirable cross-subunit disulfide bonds between the two subunits of the E172-173 dimer. Depicted in FIG. 1A are the simulated time-dependent Cα-Cα distances for the pair of residues. Depicted in FIG. 1B is the MD-simulated E172-173 dimer structure consisting of subunits a and b. FIG. 1C is the detailed information about the MD-simulated E172-173 dimer structure concerning this important pair of residues. The interface between the two subunits is mainly composed of some residues from all of the three domains (I, II, and III) in the form of α-helices, β-sheets, and loops. L196 is located on one α-helix (E184-N197) in domain II, I301 is located on a loop in domain 1.

TABLE 1

Maximum, Minimum, and Average Cα-Cα Distances between Key Residues in the E172-173 Dimer Obtained from the 50 ns MD Simulation in Comparison with the Corresponding Cα-Cα Distances in the X-ray Crystal Structure

| E172-173 structure | | L196a-I301b | I301a-L196b |
|---|---|---|---|
| Crystal structure of E172-173[a] | | 7.29 | 7.20 |
| MD-simulated E172-173 structure (50 ns MD)[b] | Maximum | 10.85 | 7.19 |
| | Minimum | 5.16 | 4.51 |
| | Average | 7.15 | 5.44 |

[a]T172R/G173Q CocE (E172-173) crystal structure (PDB ID: 3I2F).
[b]Fully relaxed MD simulation of the E172-173 dimer structure starting from the crystal structure.

According to the locations of these residues, it is highly possible to introduce a pair of cross-subunit disulfide bonds (C196a-C301b and C301a-C196b) through the L196C/I301C mutations on E172-173. The computationally designed new mutant, i.e. the T172R/G173Q/L196C/I301C mutant (denoted as enzyme E196-301 for convenience), may have a pair of cross-subunit disulfide bonds: one between C196 of subunit a (C196a) and C301 of subunit b (C301b), and the other between C301 of subunit a (C301a) and C196 of subunit b (C196b).

It is also interesting to note that residue I301 is on a loop, implying that the loop flexibility may help to form the desirable cross-subunit disulfide bonds. In addition, molecular modeling and X-ray structural analysis (see below) of the dimer structure of the T172R/G173Q/1,196C/I301C mutant also suggested that the extra L196C/I301C mutations could slightly increase the size of the active site cavity of the enzyme and, thus, might improve the catalytic activity.

In Vitro Characterization of the Designed T172R/G173Q/L196C/I301C Mutant.

Figures 2A, 2B, 2C:
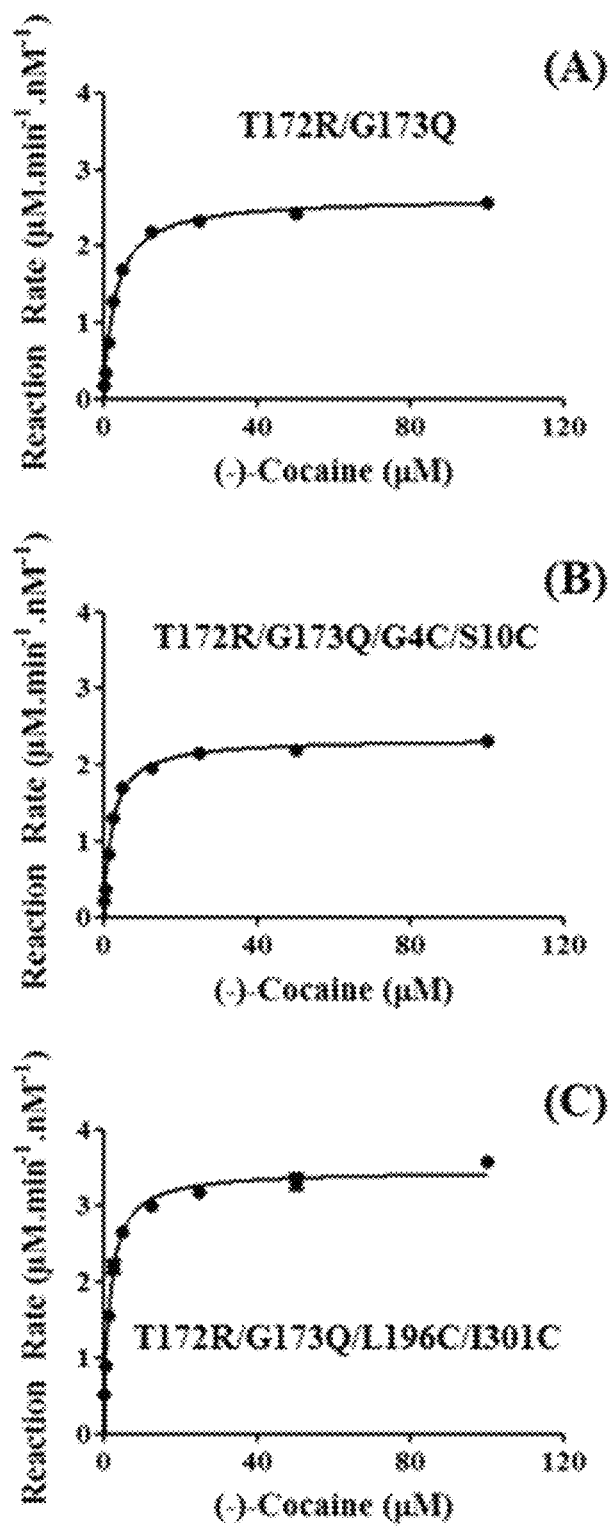
FIGS. 2A-2C show plots of measured initial reaction rates (represented in μM min-1 per nM enzyme at 37° C., with error bars) versus the substrate concentration for (−)-cocaine hydrolysis catalyzed by CocE mutants.

Based on the computational insights, the inventors carried out wet experimental tests, including site-directed mutagenesis, protein expression, purification, and enzyme activity assays on the T172R/G173Q and T172R/G173Q/1,196C/I301C mutants of CocE. For comparison, the inventors of the present disclosure also prepared and characterized the T172R/G173O/G4C/S1OC mutant which has been known to have a pair of cross-subunit disulfide bonds. (26) All of the mutants were expressed similarly well. To minimize the possible systematic experimental errors of the kinetic data, all of the three mutants were simultaneously prepared and characterized under the same experimental conditions, which allowed for fair comparison of their catalytic activity against (−)-cocaine. Michaelis-Menten kinetics of the enzymatic hydrolysis of (−)-cocaine was determined by performing the sensitive radiometric assays using [3H](−)-cocaine (labeled on its benzene ring) with varying concentrations of the substrate. Depicted in FIG. 2 are the measured kinetic data, and summarized in Table 2 are the kinetic parameters determined at 37° C.

As seen in Table 2, kcat=2600 min-1, KM=2.9 µM, and kcat/KM=9.2×108 min-1 M-1 for the T172R/G173Q mutant under the current clinical development. Compared to the T172R/G173Q mutant, the T172R/G173Q/G4C/S10C mutant has a slightly smaller kcat value (2340 min-1) and a slightly smaller KM value (2.1 µM). Overall, the catalytic efficiency (kcat/KM) changed about 20% (from 9.2×108 min−1 M−1 to 1.1×109 min−1 M−1). Interestingly, the new mutant (T172R/G173Q/L196C/I301C) designed in the present study has both a significantly increased kcat value (3450 min-1) and a significantly smaller KM value (1.5 µM). As a result, the catalytic efficiency (kcat/KM=2.3×109 min−1 M−1) of the T172R/G173Q/L196C/I301C mutant has a, ~150% improvement from that (kcat/KM=9.2×108 min−1 M−1) of the T172R/G173Q mutant under the current clinical development.

TABLE 2

Kinetic Parameters Determined for (−)-Cocaine Hydrolysis Catalyzed by the T1721t/G173Q, T172R/G173Q/G4C/S10C, and T172R/G173Q/L196C/I301C Mutants of CocEα

| CocE mutant | $k_{cat}$ (min$^{-1}$) | $K_M$ (µM) | $k_{cat}/K_M$ (min$^{-1}$ M$^{-1}$) |
|---|---|---|---|
| T172R/G173Q | 2600 | 2.9 | $9.2 \times 10^8$ |
| T172R/G173Q/G4C/S10C | 2340 | 2.1 | $1.1 \times 10^9$ |
| T172R/G173Q/L196C/I301C | 3450 | 1.5 | $2.3 \times 10^9$ |

Based on the encouraging kinetic data, the purified protein of the T172R/G173Q/L196C/I301C mutant was tested for the thermal stability at 37° C. For this purpose, the enzyme was incubated at 37° C., and the catalytic activity of the incubated enzyme against cocaine was assayed at different time points.

Figure 3:
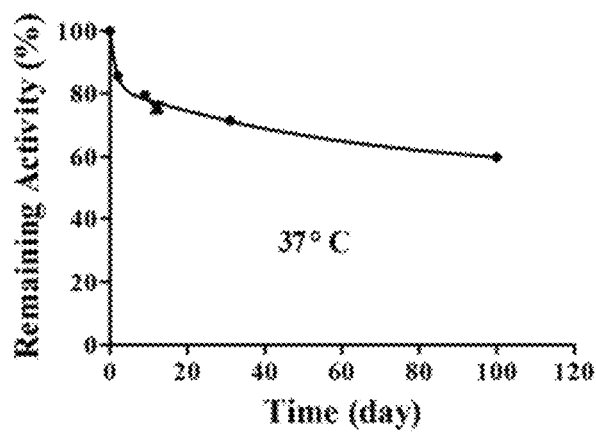
FIG. 3 provides a plot of the remaining enzyme activity of the T172R/G173Q/L196C/I301C CocE against cocaine versus the time of the enzyme incubation at 37° C. The catalytic activity of the incubated enzyme was assayed after 0, 2, 9, 12, 31, and 100 days.

As seen in FIG. 3, the enzyme showed a relatively faster decrease of the activity (around 20%) during the first a few days, compared to the last 90 days. The relatively faster decrease of the activity during the first a few days is likely due to the possibility that certain percentage of the mutant protein molecules had not yet formed the expected cross-subunit disulfide bonds before the thermal stability test. Although the cross-subunit disulfide bonds were expected to form spontaneously (as no extra oxidation reagent was employed in this study to facilitate the disulfide bond formation), a small percentage of the new mutant (T172R/G173Q/L196C/I301C) molecules did not really form the cross-subunit disulfide bonds. Those T172R/G173Q1L196C/I301C mutant molecules without the cross-subunit disulfide bonds could lose the activity more rapidly, like the T172R/G173Q mutant which has an in vitro half-life of ~6 h at 37° C. (11) However, after the first few days, the enzyme activity decreased very slowly. Within the last 90 days, the enzyme activity decreased for only, ~15%. Overall, the enzyme still retained more than 60% of the enzyme activity after incubation at 37° C. for 100 days, indicating that the in vitro half-life of the T172R/G173Q/L196C/I301C mutant at 37° C. should be longer than 100 days.

Confirmation of the Cross-Subunit Disulfide Bonds.

With the encouraging data about the significant improvement in both the catalytic activity and thermal stability at 37° C., the inventors of the present disclosure have determined the crystal structure of the T172R/G173Q/L196C/I301C mutant in order to directly confirm the formation of the cross-subunit disulfide bonds between L196C and I301C.

Figures 4A, 4B, 4C, 4D:
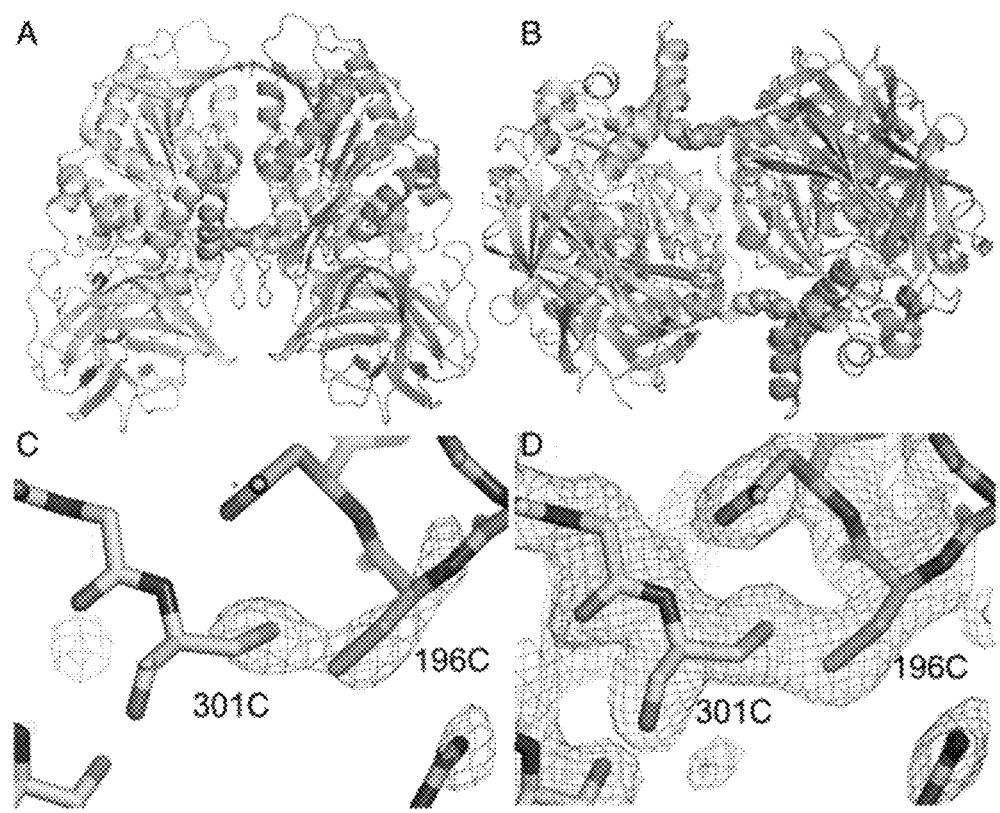
FIGS. 4A-4D depict a crystal structure of the CocE mutant dimer.

The CocE mutant crystallized with one monomer in the asymmetric unit, but a symmetry related molecule forms an extensive interface, burying over 1900 Å of solvent-accessible surface area as calculated by the PISA server. (30) The dimer formed by these two molecules (FIGS. 4A and B) corresponds to previously reported structures of unlinked (PDB 3PUH) and covalently linked (PDB 3PUI) CocE dimers. (26) Thus, the expected homodimer was formed in the crystals. Initial difference maps using the rigidly placed (without refinement) CocE mutant structure with glycine residues substituted at residue positions 196 and 301 showed strong positive Fo-Fc difference electron density for the cysteine side chains at the dimer interface (FIG. 4C) consistent with disulfide bond formation. Subsequent refinement of the model with cysteine residues introduced at these positions and no disulfide restraints gave well-defined weighted 2Fo-Fc density and excellent geometry consistent with disulfide bond formation across the subunits (FIG. 4D, see FIGS. 4A and B). The sulfur-to-sulfur distance is 2.0 Å and the dihedral angle is 94°.

In summary, the crystal structure of the enzyme unambiguously confirms the presence of the engineered intersubunit disulfide bonds. Since the dimer axis corresponds to a crystallographic 2-fold axis (space group P6522), the structure was also refined in a lower symmetry group (P65), which places a disulfide-linked dimer in the asymmetric unit and does not therefore impose symmetry on the model. This refinement resulted in geometry for the two disulfide bonds that is nearly identical to that present in the dimer on the crystallographic 2-fold axis (FIG. 8), eliminating the possibility of any artifact from this placement.

Structure-Activity Correlation.

Superposition between the X-ray crystal structures of E172-173 (representing the T172R/G173Q mutant) and E196-301 (representing the T172R/G173WL196C/I301C mutant) revealed a root-mean-square deviation (RMSD) value of 0.299 Å, indicating the high similarity of the two protein structures. However, the superposition also revealed a slight shift of two α-helices (H2 and H3 in domain II) in E196-301 compared to that in EI72-173 (see FIG. 6). The shift created a slightly enlarged active-site cavity in E196-301, which could possibly favor the catalytic reaction process. A slightly larger active site could better accommodate such a large substrate like cocaine and, thus, make the enzyme more active against cocaine; the similar type of structure-activity correlation was noted for previously designed mutants of human butyrylcholinesterase (BChE). (31) The BChE mutants with a slightly larger active site have a significantly improved catalytic efficiency against cocaine without changing substrate specificity. (31, 32)

To further understand why E196-301 has an improved catalytic activity against cocaine compared to E172-173, the present inventors performed MD simulations on the transition state (TS1) for the initial reaction step of (–)-cocaine hydrolysis catalyzed by E172-173 and E196-301. Previous computational studies 33 on the catalytic reaction mechanism for wild-type CocE-catalyzed hydrolysis of (–)-cocaine revealed that the CocE-catalyzed cocaine hydrolysis is initialized by the nucleophilic attack on the carbonyl carbon of (–)-cocaine benzoyl ester by the hydroxyl oxygen of Ser117, and that the transition state is stabilized by hydrogen bonding of the carbonyl oxygen of cocaine benzoyl ester with the hydroxyl group of Y44 side chain and the NH group of the Y118 backbone. (33) The (–)-cocaine hydrolysis catalyzed by E172-173 or E196-301 is expected to follow the same catalytic reaction mechanism, as the residues #196 and #301 are all far away from the active site. Based on the established mechanistic understanding, the stronger the hydrogen bonding of the carbonyl oxygen of the substrate with Y44 side chain and Y118 backbone, the more active the enzyme.

The general strategy and protocol for performing MD simulation on a transition state of enzymatic reaction using the classical force field have been described in detail elsewhere. (34, 35) Based on the protoco 1,34 the lengths of the transition bonds (i.e., the covalent bonds that gradually form or break during the reaction step associated with the transition state) in the transition state are restrained according to the previous QM/MM reaction-coordinate calculations, assuming that the these bond lengths do not significantly change after the mutations. The transition-state modeling in the present study was based on the inventors' QM/MM-optimized TS1 structure33 for CocE-catalyzed hydrolysis of (–)-cocaine. It is reasonable to assume that the transition bond lengths in the TS1 structure will not significantly change after the T172R/G173Q or T172R/G1730JL196C/1301C mutations. So, MD simulations were carried out on the TS1 structures corresponding to E172-173 and E196-301, with the transition bond lengths restrained.

Depicted in FIG. 7 are the simulated time-dependent H . . . O distances (relevant to the hydrogen bonds) in E172-173 and E196-301 during the MD simulations for 50 ns. The detailed analysis of the key H . . . O distances between enzyme residues and cocaine is summarized in Table 3. In E172-173, the H . . . O distance between CocO and Y44HH was 3.02 Å in maximum, 1.44 Å in minimum, and 1.87 Å in average, while the H . . . O distance between CocO and Y114H was 3.14 Å in maximum, 1.61 Å in minimum, and 2.16 Å in average. In E196-301, the H . . . O distance between Y44HH and CocO was 3.17 Å in maximum, 1.44 Å in minimum, and 1.80 Å in average, while the H . . . O distance between CocO and Y114H was 2.89 Å in maximum, 1.61 Å in minimum, and 2.13 Å in average. According to these simulated H . . . O distances, the H . . . O distances of the two hydrogen bonds in E196-301 are all shorter than the corresponding ones in E172-173, suggesting that cocaine has the stronger hydrogen bonding with E196-301 compared to that with E172-173 in the TS1 structure. The enhanced hydrogen bonding helps to stabilize the transition state (TS1) structure during the catalytic reaction process and, thus, lower the energy barrier, which explains the improved catalytic activity of the new mutant.

In Vivo Protection of Mice Against Cocaine-Induced Lethality.

For development of an effective cocaine abuse treatment using a cocaine-metabolizing enzyme, it is highly desired to have a long residence time of the enzyme in the body. To have a long residence time in the body, the enzyme must be thermostable at 37° C. for a sufficiently long time. So, it is a necessary condition, but not a sufficient condition, for an enzyme having a long residence time in the body to have a long in vitro half-life of the enzyme at 37° C. An enzyme may be eliminated rapidly from the body, even if it is very thermostable at 37° C. In this consideration, PEGylation is a popularly used strategy to prevent the possible rapid elimination of a protein from the body. Hence, the inventors further engineered E196-301 through the PEGylation modification. Activity assays confirmed that the PEGylated E196-301 completely maintained its activity against cocaine as that of E196-301.

TABLE 3

Summary of the MD-Simulated Key Distances (in Å) between the Hydrogen Atoms of Key Residue and the Carbonyl Oxygen of (−)-Cocaine Benzoyl Ester in the Rate-Determining Transition-State Structures of CocE

| Hydrogen bond | | Distances (Å) | | |
| --- | --- | --- | --- | --- |
| | | Maximum | Minimum | Average |
| Y44HH-CocO[b] | E172-173[a] | 3.02 | 1.44 | 1.87 |
| | E196-301[a] | 3.17 | 1.44 | 1.80 |
| Y118H-CocO[c] | E172-173[a] | 3.14 | 1.61 | 2.16 |
| | E196-301[a] | 2.89 | 1.61 | 2.13 |

[a]E172-173 represents T172R/G173Q CocE, and E196-301 refers to T172R/G173Q/L196C/I301C CocE.
[b]Y44HH-CocO represents the distance between the hydroxyl hydrogen (denoted as HH) of the Y44 side chain and the carbonyl oxygen (denoted as CocO) of (−)-cocaine benzoyl ester.
[c]Y118H-CocO refers to the distance between the hydrogen (H) of the Y118 backbone and the carbonyl oxygen (CocO) of (−)-cocaine benzoyl ester.

To test the ability of E196-301 (unPEGylated, unless specified otherwise) and the PEGylated E196-301 in protecting mice (n=5) from a lethal dose of cocaine, E196-301 or the PEGylated E16-301 was administered intravenously (at a single dose of 30 mg/kg) 1 min before the first intraperitoneal administration of 180 mg/kg cocaine (LD100).

Figure 5:
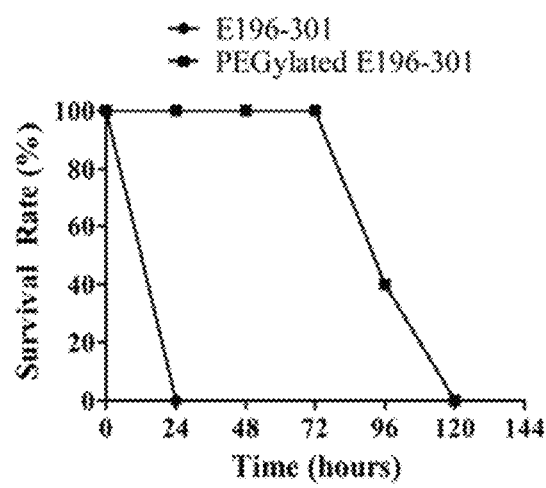
FIG. 5 illustrates the in vivo effectiveness of E196-301 (black squares) and the PEGylated E196-301 (red triangles) in the protection of mice from cocaine-induced lethality. A single dose (30 mg/kg) of E196-301 (PEGylated or unPEGylated) was administered (i.v.) 1 min before the first i.p. administration of 180 mg/kg cocaine (n=5). The mice were challenged daily with 180 mg/kg cocaine until no mouse survived. E196-301 refers to the T172R/G173Q/L196C/I301C mutant of CocE.

Depicted in FIG. 5 are the data for the in vivo protection of mice provided by E196-301 and the PEGylated E196-301 against the cocaine-induced lethality. As seen in FIG. 5, E196-301 protected the mice from death after the first injection of 180 mg/kg cocaine but lost the efficacy at the second injection of 180 mg/kg cocaine 24 hours later. The PEGylated E196-301 was able to fully protect the mice (n=5) for at least 72 hours from the acute toxicity of a lethal dose of cocaine (180 mg/kg, LD100): no mouse died after the fourth cocaine challenge at 72 hours, three mice died after the fifth cocaine challenge at 96 hours, and the remaining two mice died after the final (sixth) cocaine challenge at 120 hours (see FIG. 5). According to the data depicted in FIG. 5, the PEGylated E196-301 can protect the three mice (60%) with the protection time (tp) being between 72 and 96 h: 72 h<tp<96 h, or tp=84±12 h. For the remaining two mice (40%), 96 h<tp<120 h, or tp=108±12 h according to the data in FIG. 5. Overall, the PEGylated E196-301 can protect the mice with an average protection time (denoted as <tp> for convenience) of ~94 h, i.e. <tp>=~94 h. This is the longest in vivo protection of mice from a lethal dose of cocaine (180 mg/kg, LI3100) demonstrated so far within all in vivo studies using an exogenous enzyme.

It should be pointed out that the in vivo studies described above are a simplified animal model (using a high dose of enzyme and high doses of cocaine for convenience of animal behavior observation) to show the long residence time of the PEGylated E196-301. As discussed earlier in this report, the long residence time of the enzyme is crucial for an effective enzyme-based cocaine addiction treatment. For practical cocaine addiction treatment using a cocaine-metabolizing enzyme in humans, the cocaine doses are much lower (a typical cocaine addiction dose is ~1 mg/kg, which is much lower than the lethal dose of 180 mg/kg used in the animal model) and, correspondingly, the required dose of the enzyme for effective cocaine metabolism may be less than about 30 mg/kg.

Concluding Remarks.

Molecular dynamics simulation and subsequent structural analysis on the dimer structure of a therapeutic cocaine-metabolizing enzyme, i.e. E172-173 (which is the T172R/G173Q mutant of CocE), led to the prediction that the extra L196C/1301C mutations on E172-173 can produce cross-subunit disulfide bonds in the dimer. The formation of cross-subunit disulfide bonds were expected to stabilize the dimer structure and also improve the catalytic activity against cocaine.

Following the computational prediction, in vitro experimental studies have demonstrated that the computationally designed new CocE mutant (T172R/G173Q/L196C/1301C), i.e. E196-301, indeed has a significantly improved catalytic efficiency against cocaine and a considerably extended in vitro half-life (>100 days) at 37° C.

The predicted cross-subunit disulfide bonds in the E196-301 dimer structure were confirmed by X-ray diffraction. In addition, in vivo studies in mice demonstrated that the PEGylated E196-301 can fully protect mice from a lethal dose of cocaine (180 mg/kg, LD100) for at least 3 days, with the average protection time being about 94 hours. All of the data suggests that the currently designed enzyme E196-301 with improved thermal stability and catalytic activity against cocaine is more valuable than the existing therapeutic enzyme E172-173, which is under clinical trial phase II for cocaine overdose treatment. The encouraging outcomes of this study also suggest that the structure-and-mechanism-based computational design and integrated computational-experimental approach are promising for rational protein drug design. The general computational protein design strategy and approach to simultaneously improve both the protein stability and function may also be valuable for engineering other proteins. Intermonomer disulfide bonds in the CocE mutant (E196-301) dimer refined in space group P65 is shown in FIG. 8.

Material and Methods

Computational Methods Used for the Mutant Design.

For the molecular dynamics (MD) simulations on the CocE dimer structures, the starting structure of the E172-173 dimer was the X-ray crystal structure (deposited in the Protein Data Bank) at 2.0 Å resolution (PDB ID: 3I2F) (26) and the starting structure of the E196-301 dimer was the X-ray crystal structure determined in the present study. In order to simulate the TS1 structures for the enzymatic hydrolysis of cocaine, the transition bond lengths in the TS1 structure were restrained as those in previously QM/MM-optimized TS1 structure33 for CocE-catalyzed hydrolysis of (−)-cocaine. A transition bond in the TS1 structure refers to a covalent bond which gradually forms or breaks in the transition state (TS1) during the first step of the chemical reaction process. According to previously reported QM/MM reaction-coordinate calculations33 on CocE-catalyzed hydrolysis of (−)-cocaine, there are three transition bonds in the TS1 structure: (1) the internuclear distance (1.93 Å) between the carbonyl carbon of (−)-cocaine benzoyl ester and the hydroxyl oxygen (Oγ) of Ser117 side chain; (2) the internuclear distance (1.38 Å) between the hydroxyl oxygen (Oγ) and hydroxyl hydrogen (Hγ) of Ser117 side chain; (3) the internuclear distance (1.19 Å) between the hydroxyl hydrogen (Hγ) of Ser117 side chain and the nitrogen (Nε) atom of His287 side chain. These three transition bond lengths were used in all of the MD simulations on the TS1 structures. All of the mutations (T172R/G173Q and L196C/I301C) examined in the present study were made on the amino acid residues (#172, #173, #196, and #301) that are far away from the active site. So, these mutations are not expected to dramatically change the catalytic mechanism or significantly affect the transition bond lengths. The similar approximation was used in previously reported computational modeling studies (34, 36) on other esterases, leading to successful design and discovery of new mutants with a significantly improved catalytic activity.

The general procedure for carrying out the MD simulations in the present study was similar to that used in previously-reported computational studies (34, 37-39) Briefly, all molecular mechanics-based energy minimization and MD simulations were carried out by using the AMBER 9 program package. The Amber force field (ff03) was used to establish the potentials of protein 40 For each system, counterions (Na) were used to neutralize the system and, then, the neutralized system was immersed in an orthorhombic box of TIP3P water molecules 41 with a minimum solute-wall distance of 10 Å. The whole system was carefully equilibrated and fully energy-minimized. After that, the system was gradually heated in the NPT ensemble from 10 to 300 K over 60 ps. Then, a 50 ns MD simulation was performed under the normally adopted temperature (300 K). During the MD simulation, the Particle Mesh Ewald (PME) method was employed to deal with the long-range electrostatic interactions. 42 The SHAKE procedure was applied to constrain the lengths of all covalent bonds involving hydrogen atoms, 43 with a time step of 2.0 fs. The atomic coordinates were saved every 1 ps for subsequent sampling and analysis.

Site-Directed Mutagenesis.

Point mutations were generated using the QuikChange method. (44) Further mutations required to produce a new CocE mutant cDNA were generated from the cDNA corresponding to the E172-173 in the pET-22b (+) bacterial expression vector. All mutants were sequenced in both directions over the entire coding region. Using plasmid DNA as template and primers with specific base-pair alterations, mutations were made by polymerase chain reaction with Pfu DNA polymerase for replication fidelity. The PCR product was treated with DpnI endonuclease to digest the parental DNA template. The digested product was transformed into *Escherichia coli*, amplified, and purified. The DNA sequences of the mutants were confirmed by DNA sequencing.

Protein Expression and Purification.

The CocE mutants were expressed in *Escherichia coli* BL-21 (DE3) cells grown at 37° C. Protein expression was induced with 1 mM isopropyl-β-thiogalactopyranoside (Sigma-Aldrich) for about 15 h at 18° C. Cells were pelleted, resuspended in 50 mM Tris-HCl, pH 8.0, 150 mM NaCl buffer with protease inhibitor cocktail (Sigma) and lysed using a French press (Thermo Fisher Scientific). The 6His-tagged enzymes were then enriched using HisPur cobalt resin (Thermo Fisher Scientific). The eluted fractions were concentrated by using an Amicon Ultra-50K centrifuge (Millipore, Billerica, Mass.). The enzyme concentrations were determined using a CB-Protein Assay kit (from CAL-BIOCHEM) with bovine serum albumin as a standard.

Enzyme Activity Assays.

To measure (−)-cocaine and benzoic acid, the product of (−)-cocaine hydrolysis catalyzed by BChE, sensitive radiometric assays were used based on toluene extraction of [3H](−)-cocaine labeled on its benzene ring. (45) In brief, to initiate the enzymatic reaction, 100 nCi of [3H](−)-cocaine was mixed with the solution of the purified enzyme. The enzymatic reactions proceeded at 37° C. with varying concentrations of (−)-cocaine. The reactions were stopped by adding 200 μL of 0.1 M HCl, which neutralized the liberated benzoic acid whereas ensuring a positive charge on the residual (−)-cocaine. [3H]Benzoic acid was extracted by 1 mL of toluene and measured by scintillation counting. Finally, the measured (−)-cocaine concentration-dependent radiometric data were analyzed by using the standard Michaelis-Menten kinetics with Prism 5 (GraphPad Software Inc., San Diego, Calif.).

To determine the in vitro half-life of the enzyme at 37° C., the enzyme was diluted to 200 μg/mL, stored in sealed glass tubes and incubated at 37° C. The tubes were sealed to avoid the possible vaporization-associated change in the volume. One tube will be taken out of the incubation cabinet at various time points (0, 2, 9, 12, 31, and 100 days) and assayed for the catalytic activity against (−)-cocaine as mentioned above. The percentage of remaining activity was plotted against the incubation time.

Crystallization and Structure Determination.

Crystals of the designed new mutant of CocE were grown by hanging drop vapor diffusion, screening for conditions against the JCSG Core Suite (Qiagen). At a protein concentration of 10 mg rnL-1 and 1:1 well-to-protein ratio, several screen conditions gave spindle-shaped or fusiform crystals. The most ordered crystals grew against wells containing 0.1 M phosphate-citrate (pH 4.2), 1.6 M sodium dihydrogen phosphate, and 0.4 M dipotassium hydrogen phosphate (JCSG IV #94). The largest crystals were ~0.2 mm in the longest dimension.

Crystals were mounted in Mylar loops (LithoLoops, Molecular Dimensions) and flash frozen (46) in liquid nitrogen after passing for a few seconds through a solution containing the well solutes plus 20% glycerol. X-ray data were collected at beamline 22ID (SER-CAT sector) at the Advanced Photon Source, Argonne National Laboratory at a temperature of 110 K. Data were reduced with the program HKL2000 (47) and all aspects of structure determination and refinement were carried out in the Phenix suite. (48) Initial phasing was done by molecular replacement (Phaser (49) module) using the structure of unliganded cocaine esterase 25 (PDB code 3I2J). Subsequent model refinement and addition of ordered solvent was carried out using the auto-build and refinement modules of Phenix with manual rebuilding in Coot, (50) which was also used to introduce the sequence changes into the model (T172R, G173Q L196C, and I301C). Data reduction and model parameters are given in Table 4.

PEGylation.

Purified enzyme was conjugated with maleimide-linked branched poly(ethylene glycol) (PEG) with molecular weight of 40 kDa (JenKem Technology, Allen, Tex.) overnight in PBS buffer, pH 7.4 at the PEG to enzyme molar ratio of 20. The PEGylated protein was purified by using the same HisPur cobalt resin mentioned above.

In Vivo Studies.

Male CD-1 mice (25-30 g) were purchased from Harlan (Indianapolis, Ind.) and were housed in groups of four mice per cage. All mice were allowed ad libitum access to food and water and were maintained on a 12 h light-dark cycle with lights on at 6:30 a.m. in a room kept at a temperature of 21-22° C. Experiments were performed in accordance with the Guide for the Care and Use of Laboratory Animals as adopted and promulgated by the National Institutes of Health. The experimental protocols were approved by the Institutional Animal Care and Use Committee (IACUC) at the University of Kentucky.

The purified enzyme was administrated intravenously (i.v., via tail vein) and (−)-cocaine HCl (obtained from National Institute on Drug Abuse, Bethesda, Md.) was administered intraperitoneally, at a volume of about 0.2 mL/mouse. Cocaine-induced toxicity was characterized by the occurrence of lethality. Lethality was defined as cessation of observed movement and respiration. A single dose (30 mg/kg) of E196-301 with or without the PEGylation was administered intravenously (i.v.) 1 min before the first intraperitoneal (i.p.) administration of 180 mg/kg cocaine (n=5). Then, the mice were challenged again daily with 180 mg/kg cocaine (i.p.) until no mouse survived. Following cocaine administration, mice were immediately placed individually for observation. The presence or absence of lethality was recorded for 60 min following cocaine administration.

Figure 6:
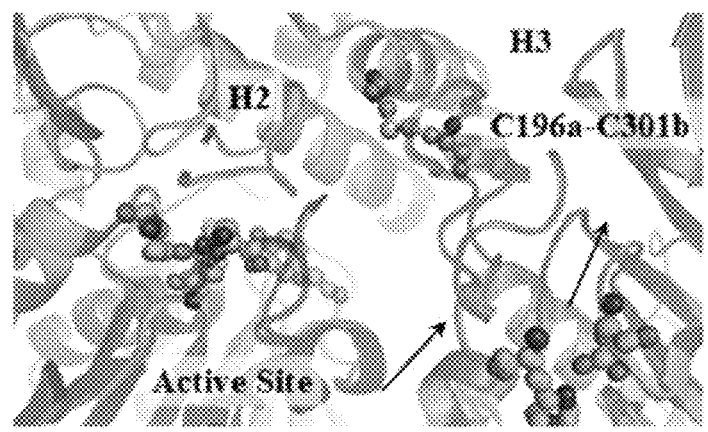
FIG. 6 illustrates backbone superposition between the X-ray crystal structures of E172-173 and E196-301. E172-173 is represented in green ribbons, and E196-301 is represented in red ribbons. The black arrow indicates the shift direction. Here, E172-173 represents T172R/G173Q CocE, and E196-301 refers to T172R/G173Q/L196C/I301C CocE.

X-ray crystallography data collection and refinement statistics are provided in Table 4. Backbone superposition between the X-ray crystal structures of E172-173 and E196-301 is depicted in FIG. 6. Intermonomer disulfide bonds in the CocE mutant (E196-301) dimer refined in space group P65 (FIG. 8). This material is available free of charge via the Internet at pubs.acs.org. Accession Codes The atomic coordinates and structure factors (code 4P08) for the crystal structure of the T172R/G173O/L196C/1301C mutant of CocE have been deposited in the Protein Data Bank, Research Collaborator), for Structural Bioinformatics, Rutgers University, New Brunswick, N.J.

TABLE 4

Data collection and refinement statistics.

| | |
|---|---|
| Wavelength (Å) | 1.0 |
| Resolution range (Å) | 50-2.34 (2.42-2.34)[a] |
| Space group | P 6$_5$22 |
| Unit cell | a = b = 106.6 Å c = 220.532 Å |
| | α = β = 90° c = 120° |
| Total reflections | 561710 |
| Unique reflections | 31943 |
| Multiplicity | 17.5 (9.9) |
| Completeness (%) | 99.73 (97.41) |
| Mean I/sigma(I) | 17.71 (2.70) |
| Wilson B-factor | 28.84 |
| R-sym | 0.161 (0.956) |
| R-factor | 0.1769 (0.2488) |
| R-free | 0.2208 (0.3348) |
| Number of atoms | 4793 |
| macromolecules | 4364 |
| water | 429 |
| Protein residues | 571 |
| RMS(bonds) | 0.005 |
| RMS(angles) | 0.89 |
| Ramachandran favored (%) | 95 |
| Ramachandran outliers (%) | 0 |
| Clashscore | 5.37 |
| Average B-factor | 27.80 |
| macromolecules | 27.40 |
| solvent | 31.80 |

[a]Statistics for the highest-resolution shell are shown in parentheses.

INCORPORATION BY REFERENCE

All publications, patents, and patent applications mentioned in this specification are herein incorporated by reference to the same extent as if each individual publication, patent, or patent application was specifically and individually indicated to be incorporated by reference.

It will be understood that various details of the present disclosure can be changed without departing from the scope of the subject matter disclosed herein. Furthermore, the foregoing description is for the purpose of illustration only, and not for the purpose of limitation.

Throughout this document, various references are mentioned. All such references are incorporated herein by reference, including the references set forth in the following list:

(1) UNODC. (2010) World Drug Report 2010, United Nations Publication, Sales No. E.10.XI.13.

(2) Karila, L., Gorelick, D., Weinstein, A., Noble, F., Benyamina, A., Coscas, S., Blecha, L., Lowenstein, W., Martinot, J. L., Reynaud, M., and Lepine, J. P. (2008) New treatments for cocaine dependence: A focused review. Int. J. Neuropsychoph. 11, 425-438.

(3) Xi, Z.-X., and Gardner, L. E. (2008) Hypothesis-driven medication discovery for the treatment of psychostimulant addiction. Curr. Drug Abuse Rev. 1, 303-327.

(4) Carrera, M. R. A., Kaufmann, G. F., Mee, J. M., Meijler, M. M., Koob, G. F., and Janda, K. D. (2004) Treating cocaine addiction with viruses. Proc. Natl. Acad. Sci. U.S.A. 101, 10416-10421.

(5) Kamendulis, L. M., Brzezinski, M. R, Pindel, E. V., Bosron, W. F., and Dean, R. A. (1996) Metabolism of cocaine and heroin is catalyzed by the same human liver carboxylesterases. J. Pharmacol. Exp. Ther. 279, 713-717.

(6) Meijler, M. M., Kaufmann, G. F., Q, L., Mee, J. M., Coyle, A. R., Moss, J. A., Wirsching, P., Matsushita, M., and Janda, K. D. (2005) Fluorescent cocaine probes: A tool for the selection and engineering of therapeutic antibodies. J. Am. Chem. Soc. 127, 2477-2484.

(7) Zhan, C.-G., Deng, S.-X., Skiba, J. G., Hayes, B. A., Tschampel, S. M., Shields, G. C., and Landry, D. W. (2005) First-principle studies of intermolecular and intramolecular catalysis of protonated cocaine. J. Comput. Chem. 26, 980-986.

(8) Landry, D. W., Zhao, K., Yang, G. X., Glickman, M., and Georgiadis, T. M. (1993) Antibody-catalyzed degradation of cocaine. Science 259, 1899-1901.

(9) Larsen, N. A., Turner, J. M., Stevens, J., Rosser, S. J., Basran, A., Lerner, R. A., Bruce, N. C., and Wilson, I. A. (2002) Crystal structure of a bacterial cocaine esterase. Nat. Struct. Mol. Biol. 9, 17-21.

(10) Ko, M.-C., Bowen, L. D., Narasimhan, D., Berlin, A. A., Lukacs, N. W., Sunahara, R K., Cooper, Z. D., and Woods, J. H. (2007) Cocaine esterase: Interactions with cocaine and immune responses in mice. J. Pharmacol. Exp. Ther. 320, 926-933.

(11) Gao, D., Narasimhan, D. L., Macdonald, J., Ko, M.-C., Landry, D. W., Woods, J. H., Sunahara, R. K., and Zhan, C.-G. (2009) Thermostable variants of cocaine esterase for long-time protection against cocaine toxicity. Mol. Pharmacol. 75, 318-323.

(12) Sticke, D. F., Presta, L. G., Dill, K. A., and Rose, G. D. (1992) Hydrogen bonding in globular proteins. J. Mol. Biol. 226, 1143-1159.

(13) ICabashima, T., Li, Y., Kanada, N., Ito, K., and Yoshimoto, T. (2001) Enhancement of the thermal stability of pyroglutamyl peptidase I by introduction of an intersubunit disulfide bond. Biochim. Biophys. Acta 1547, 214-220.

(14) Shoichet, B. K., Baase, W. A., Kurold, R, and Matthews, B. W. (1995) A relationship between protein stability and protein function. Proc. Natl. Acad. Sci. U.S.A. 92, 452-456.

(15) Bjork, A., Dalhus, B., Mantzilas, D., Eij sink, V. G. H., and Sire*, R. (2003) Stabilization of a tetrameric malate dehydrogenase by introduction of a disulfide bridge at the dimer-dieter interface. J. Mol. Biol. 334, 811-821.

(16) Han, Z.-l., Han, S.-y., Zheng, S.-p., and Lin, Y. (2009) Enhancing thermostability of a Rhizonnicor miehei lipase by engineering a disulfide bond and displaying on the yeast cell surface. Appl. Microbiol. Biotechnol. 85, 117-126.

(17) Beadle, B. M., and Shoichet, B. K. (2002) Structural bases of stability-function tradeoffs in enzymes. J. Mol. Biol. 321, 285-296.

(18) Bloom, J. D., Wilke, C. O., Arnold, F. H., and Adami, C. (2004) Stability and the evolvability of function in a model protein. Biophys. J. 86, 2758-2764.

(19) Nagatani, R. A., Gonzalez, A., Shoichet, B. K., Brinen, L. S., and Babbitt, P. C. (2007) Stability for function trade-offs in the enolase superfamily "catalytic module". Biochemistry 46, 6688-6695.

(20) Tokuriki, N., Stricher, F., Serrano, L., and Tawfik, D. S. (2008) How protein stability and new functions trade off PLoS Comput. Biol. 4, e1000002.

(21) Thomas, V. L., McReynolds, A. C., and Shoichetb, B. K. (2010) Structural bases for stability-function tradeoffs in antibiotic resistance. J. Mol. Biol. 396, 47-59.

(22) Merski, M., and Shoichet, B. K. (2012) Engineering a model protein cavity to catalyze the Kemp elimination. Proc. Natl. Acad. Sci. U.S.A. 109, 16179-16183.

(23) Brim, R. L., Nance, M. R, Youngstrom, D. W., Narasimhan, D., Zhan, C.-G., Tesmer, J. J., Sunahara, R. K., and Woods, J. H. (2010) A thermally stable form of bacterial cocaine esterase: A potential therapeutic agent for treatment of cocaine abuse. Mol. Pharmacol. 77, 593-600.

(24) Collins, G. T., Brim, R. L., Narasimhan, D., Ko, M.-C., Sunahara, R. K., Zhan, C.-G., and Woods, J. H. (2009) Cocaine esterase prevents cocaine-induced toxicity and the ongoing intravenous self-administration of cocaine in rats. J. Pharmacol. Exp. They. 331, 445-455.

(25) Narasimhan, D., Nance, M. R., Gao, D., Ko, M.-C., Macdonald, J., Tamburi, P., Yoon, D., Landry, D. M., Woods, J. H., Zhan, C.-G., Tesmer, J. J. G., and Sunahara, R K. (2010) Structural analysis of thermostabilizing mutations of cocaine esterase. Protein. Eng. Des. Sel. 23, 537-547.

(26) Narasimhan, D., Collins, G. T., Nance, M. R., Nichols, J., Edwald, E., Chan, J., Ko, M.-C., Woods, J. H., Tesmer, J. J. G., and Sunahara, R. K. (2011) Subunit stabilization and polyethylene glycolation of cocaine esterase improves in vivo residence time. Mol. Pharmacol. 80, 1056-1065.

(27) Collins, G. T., Zaks, M. E., Cunningham, A. R., St Clair, C., Nichols, J., Narasimhan, D., Ko, M.-C., Sunahara, R. K., and Woods, J. H. (2011) Effects of a long-acting mutant bacterial cocaine esterase on acute cocaine toxicity in rats. Drug Alcohol Depend. 118, 158-165.

(28) Collins, G. T., Narasimhan, D., Cunningham, A. R., Zaks, M. E., Nichols, J., Ko, M.-C., Sunahara, R. K., and Woods, J. H. (2012) Longlasting effects of a PEGylated mutant cocaine esterase (CocE) on the reinforcing and discriminative stimulus effects of cocaine in rats. Neuropsychopharmacology 37, 1092-1103.

(29) Collins, G. T., Brim, I L L., Noon, K. R., Narasimhan, D., Lukacs, N. W., Sunahara, R. K., Woods, J. H., and Ko, M.-C. (2012) Repeated administration of a mutant cocaine esterase: Effects on plasma cocaine levels, cocaine-induced cardiovascular activity, and immune responses in rhesus monkeys. J. Pharmacol. Exp. Ther. 342, 205-213.

(30) Krissinel, E., and Henrick, K. (2007) Inference of macromolecular assemblies from crystalline state. J. Mol. Biol. 372, 774-797.

(31) Yang, W., Pan, Y., Zheng, F., Cho, H., Tai, H.-H., and Zhan, C. G. (2009) Free-energy perturbation simulation on transition states and redesign of butyrylcholinesterase. Biophys. J. 96, 1931-1938.

(32) Hou, S., Xue, L, Yang, W., Fang, L., Zheng, F., and Zhan, C.-G. (2013) Substrate selectivity of high-activity mutants of human butyrylcholinesterase. Org. BiotnoL Chem. 11, 7477-7485.

(33) Liu, J., Hamza, A., and Zhan, C.-G. (2009) Fundamental reaction mechanism and free energy profile for (−)-cocaine hydrolysis catalyzed by cocaine esterase. J. Am. Chem. Soc. 131, 11964-11975.

(34) Pan, Y., Gao, D., Yang, W., Cho, H., Yang, G., Tai, H.-H., and Zhan, C.-G. (2005) Computational redesign of human butyrylcholinesterase for anticocaine medication. Proc. Natl. Acad. Sci. U.S.A. 102, 16656-16661.

(35) Zheng, F., Yang, W., Xue, L., Hou, S., Liu, J., and Zhan, C.-G. (2010) Design of high-activity mutants of human butyrylcholinesterase against (−)-cocaine: structural and energetic factors affecting the catalytic efficiency. Biochemistry 49, 9113-9119.

(36) Gao, D., and Zhan, C.-G. (2006) Modeling evolution of hydrogen bonding and stabilization of transition states in the process of cocaine hydrolysis catalyzed by human butyrylcholinesterase. Proteins 62, 99-110.

(37) Hamza, A, Cho, H., Tai, H. H., and Zhan, C.-G. (2005) Molecular dynamics simulation of cocaine binding with human butyrylcholinesterase and its mutants. J. Phys. Chem. B 109, 4776-4782.

(38) Pan, Y., Gao, D., Yang, W., Cho, H., and Zhan, C.-G. (2007) Free energy perturbation (FEP) simulation on the transition states of cocaine hydrolysis catalyzed by human butyrylcholinesterase and its mutants. J. Am. Chem. Soc. 129, 13537-13543.

(39) Zheng, F., Yang, W., Ko, M.-C., Liu, J., Cho, H., Gao, D., Tong, M., Tai, H.-H., Woods, J. H., and Zhan, C.-G. (2008) Most efficient cocaine hydrolase designed by virtual screening of transition states. J. Am. Chem. Soc. 130, 12148-12155.

(40) Yong, D., Chun, W., Shibasish, C., Mathew, C. L., Guoming, X., Wei, Z., Rong, Y., Piotr, C., Ray, L., Taisung, L., James, C., Junmei, W., and Peter, K. (2003) A point-charge force field for molecular mechanics simulations of proteins based on condensed-phase quantum mechanical calculations. J. Comput. Chem. 24, 1999-2012.

(41) Jorgensen, W. L., Chandrasekhar, J., Madura, J. D., Impey, R. W., and Klein, M. L. (1983) Comparison of simple potential functions for simulating liquid water. J. Chem. Phys. 79, 926-935.

(42) Darden, T., York, D., and Pedersen, L. (1993) Particle mesh Ewald: An N [center-dot] log (N) method for Ewald sums in large systems. J. Chem. Phys. 98, 10089-10092.

(43) Ryckaert, J.-P., Ciccotti, G., and Berendsen, H. J. C. (1977) Numerical integration of the cartesian equations of

(44) Braman, J., Papworth, C., and Greener, A (2000) Site-directed mutagenesis using double-stranded plasmid DNA templates. Nucleic Acid Protocols Handbook, 835-844.
(45) Sun, H., Shen, M. L., Pang, Y.-P., Lockridge, O., and Brimijoin, S. (2002) Cocaine metabolism accelerated by a re-engineered human butyrylcholinesterase. J. Pharmacol. Exp. Ther. 302, 710-716.
(46) Rodgers, D. W. (1997) Practical cryocrystallography, in Methods in Enzymology (Charles, W. Carter, Jr., Ed.), pp 183-203, Academic Press, New York.
(47) Otwinowsld, Z., and Minor, W. (1997) Processing of X-ray diffraction data collected in oscillation mode, in Methods in Enzymology (Charles, W. Carter, Jr., Ed.), pp 307-326, Academic Press, New York.
(48) Adams, P. D., Afonine, P. V., Bunkoczi, G., Chen, V. B., Davis, I. W., Echols, N., Headd, J. J., Hung, L.-W., Kapral, G. J., Grosse-Kunstleve, R. W., McCoy, A. J., Moriarty, N. W., Oeffirer, R., Read, R. J., Richardson, D. C., Richardson, J. S., Terwilliger, T. C., and Zwart, P. H. (2010) PHENIX: A comprehensive Python-based system for macromolecular structure solution. Acta Crystallogr. D 66, 213-221.
(49) McCoy, A J., Grosse-Kunstleve, R. W., Adams, P. D., Winn, M. D., Storoni, L. C., and Read, R. J. (2007) Phaser crystallographic software. J. Appl. Crystallogr. 40, 658-674.
(50) Emsley, P., and Cowtan, K. (2004) Coot: Model-building tools for molecular graphics. Acta Crystallogr. D 60, 2126-2132.

---

SEQUENCES

SEQ ID NO: 1

```
   1                                                                                       90
ATGGTGGACGGGAATTACAGTGTTGCCTCGAACGTGATGGTTCCGATGCGTGATGGGGTGCGTCTGGCGGTCGACCTGTACCGACCAGAT
  91                                                                                      180
GCTGATGGACCTGTTCCGGTCCTGCTGGTTCGCAACCCATACGACAAGTTCGACGTGTTCGCGTGGTCGACGCAGTCGACAAACTGGCTT
 181                                                                                      270
GAGTTCGTGCGTGATGGCTATGCCGTGGTCATTCAAGACACGCGTGGCTTGTTCGCATCGGAAGGTGAGTTCGTCCCGCACGTTGACGAC
 271                                                                                      360
GAAGCTGACGCCGAGGATACGTTGAGCTGGATTCTGGAACAAGCGTGGTGCGACGGCAATGTGGGCATGTTCGGCGTTTCGTACTTGGGT
 360                                                                                      450
GTGACCCAGTGGCAGGCCGCCGTATCCGGCGTTGGTGGGCTGAAGGCGATCGCGCCGTCCATGGCGTCGGCGGACTTGTACCGCGCCCCG
 450                                                                                      540
TGGTACGGCCCTGGTGGTGCGCTTTCAGTCGAGGCGCTGTTGGGCTGGTCAGCTCTCATAGGTACTGGGCTCATCACGTCGAGGTCTGAC
 541                                                                                      630
GCCCGGCCCGAAGACGCAGCCGACTTCGTCCAACTCGCAGCAATTCTCAATGACGTCGCTGGCGCGGCGTCGGTCACGCCCCTGGCCGAG
 631                                                                                      720
CAACCGCTTCTGGGCCGACTGATTCCGTGGGTGATCGATCAGGTTGTCGATCACCCCGACAACGATGAATCATGGCAGTCCATTAGCTTG
 721                                                                                      810
TTTGAACGACTCGGCGGGTTGGCAACACCGGCCTTGATCACGGCTGGGTGGTACGACGGGTTCGTCGGCGAATCGTTGCGCACTTTCGTT
 811                                                                                      900
GCGGTCAAGGACAATGCCGACGCACGTTTGGTTGTCGGCCCTTGGAGTCACAGCAACCTCACTGGTCGGAATGCGGACCGGAAGTTCGGC
 901                                                                                      990
ATTGCCGCGACCTACCCGATTCAAGAAGCCACCACGATGCACAAGGCATTCTTCGACCGGCACCTCCGCGGCGAGACCGATGCACTCGCA
 991                                                                                     1080
GGCGTCCCCAAAGTGCGGCTGTTCGTAATGGGCATCGATGAGTGGCGTGACGAAACGGACTGGCCACTGCCGGACACGGCGTATACGCCC
1081                                                                                     1170
TTCTATCTTGGAGGTAGCGGGGCTGCGAATACCTCCACGGGTGGTGGAACACTGTCGACGTCGATTTCCGGAACTGAATCTGCTGACACC
1171                                                                                     1260
TACCTGTATGATCCGGCCGATCCCGTGCCTTCGCTCGGGGGACGCTGCTGTTCCACAACGGAGACAACGGACCCGCCGACCAACGTCCC
1261                                                                                     1350
ATTCATGACCGGGACGACGTGTTGTGTTACAGCACTGAGGTATTGACCGACCCGGTGGAAGTAACCGGCACCGTCTCCGCCCGGCTGTTC
1351                                                                                     1440
GTGTCGTCATCAGCGGTGGACACTGATTTCACCGCCAAACTTGTCGACGTATTTCCCGACGGTCGCGCGATCGCGCTGTGACGGGATC
1441                                                                                     1530
GTGCGGATGCGGTACCGCGAGACGTTGGTCAATCCAACCTTGATCGAAGCGGGCGAAATCTACGAGGTTGCTATCGACATGCTTGCAACC
1531                                                                                     1620
TCGAATGTATTCCTGCCAGGGCATCGCATCATGGTCCAAGTATCAAGTAGCAACTTCCCGAAATACGACCGCAATTCGAATACCGGCGGA
```

| SEQUENCES |
| --- |
| 1621<br>1710<br>GTAATCGCACGGGAACAGCTCGAAGAGATGTGCACCGCCGTGAACCGCATTCACCGAGGACCTGAGCATCCCAGCCACATTGTGCTGCCG<br>1711<br>ATTATCAAGCGA<br><br>SEQ ID NO: 2<br>1                                 60<br>MVDGNYSVASNVMVPMRDGVRLAVDLYRPDADGPVPVLLVRNPYDKFDVFAWSTQSTNWL<br>61                          120<br>EFVRDGYAVVIQDTRGLFASEGEFVPHVDDEADAEDTLSWILEQAWCDGNVGMFGVSYLG<br>121                        180<br>VTQWQAAVSGVGGLKAIAPSMASADLYRAPWYGPGGALSVEALLGWSALIG<u>TG</u>LITSRSD<br>181                        240<br>ARPEDAADFVQLAAI<u>L</u>NDVAGAASVTPLAEQPLLGRLIPWVIDQVVDHPDNDESWQSISL<br>241                        300<br>FERLGGLATPALITAGWYDGFVGESLRTFVAVKDNADARLVVGPWSHSNLTGRNADRKFG<br>301                        360<br><u>I</u>AATYPIQEATTMHKAFFDRHLRGETDALAGVPKVRLFVMGIDEWRDETDWPLPDTAYTP<br>361                        420<br>FYLGGSGAANTSTGGGTLSTSISGTESADTYLYDPADPVPSLGGTLLFHNGDNGPADQRP<br>421                        480<br>IHDRDDVLCYSTEVLTDPVEVTGTVSARLFVSSSAVDTDFTAKLVDVFPDGRAIALCDGI<br>481                        540<br>VRMRYRETLVNPTLIEAGEIYEVAIDMLATSNVFLPGHRIMVQVSSSNFPKYDRNSNTGG<br>541<br>VIAREQLEEMCTAVNRIHRGPEHPSHIVLPIIKR<br>Note: Residues labeled in red are: T172, G173, L196, and I301<br><br>SEQ ID NO: 3<br>T172R/G173Q/L196C/I301C CocE<br>1<br>90<br>ATGGTGGACGGGAATTACAGTGTTGCCTCGAACGTGATGGTTCCGATGCGTGATGGGGTGCGTCTGGCGGTCGACCTGTACCGACCAGAT<br>91<br>180<br>GCTGATGGACCTGTTCCGGTCCTGCTGGTTCGCAACCCATACGACAAGTTCGACGTGTTCGCGTGGTCGACGCAGTCGACAAACTGGCTT<br>181<br>270<br>GAGTTCGTGCGTGATGGCTATGCCGTGGTCATTCAAGACACGCGTGGCTTGTTCGCATCGGAAGGTGAGTTCGTCCCGCACGTTGACGAC<br>271<br>360<br>GAAGCTGACGCCGAGGATACGTTGAGCTGGATTCTGGAACAAGCGTGGTGCGACGGCAATGTGGGCATGTTCGGCGTTTCGTACTTGGGT<br>360<br>450<br>GTGACCCAGTGGCAGGCCGCCGTATCCGGCGTTGGTGGGCTGAAGGCGATCGCGCCGTCCATGGCGTCGGCGGACTTGTACCGCGCCCCG<br>450<br>540<br>TGGTACGGCCCTGGTGGTGCGCTTTCAGTCGAGGCGCTGTTGGGCTGGTCAGCTCTCATAGGT<u>CGCCAG</u>CTCATCACGTCGAGGTCTGAC<br>541<br>630<br>GCCCGGCCCGAAGACGCAGCCGACTTCGTCCAACTCGCAGCAATT<u>TGC</u>AATGACGTCGCTGGCGCGGCGTCGGTCACGCCCCTGGCCGAG<br>631<br>720<br>CAACCGCTTCTGGGCCGACTGATTCCGTGGGTGATCGATCAGGTTGTCGATCACCCCGACAACGATGAATCATGGCAGTCCATTAGCTTG<br>721<br>810<br>TTTGAACGACTCGGCGGGTTGGCAACACCGGCCTTGATCACGGCTGGGTGGTACGACGGGTTCGTCGGCGAATCGTTGCGCACTTTCGTT<br>811<br>900<br>GCGGTCAAGGACAATGCCGACGCACGTTTGGTTGTCGGCCCTTGGAGTCACAGCAACCTCACTGGTCGGAATGCGGACCGGAAGTTCGGC<br>901<br>990<br><u>TGC</u>GCCGCGACCTACCCGATTCAAGAAGCCACCACGATGCACAAGGCATTCTTCGACCGGCACCTCCGCGGCGAGACCGATGCACTCGCA<br>991<br>1080<br>GGCGTCCCCAAAGTGCGGCTGTTCGTAATGGGCATCGATGAGTGGCGTGACGAAACGGACTGGCCACTGCCGGACACGGCGTATACGCCC<br>1081<br>1170<br>TTCTATCTTGGAGGTAGCGGGGCTGCGAATACCTCCACGGGTGGTGGAACACTGTCGACGTCGATTTCCGGAACTGAATCTGCTGACACC<br>1171<br>1260<br>TACCTGTATGATCCGGCCGATCCCGTGCCTTCGCTCGGGGGACGCTGCTGTTCCACAACGGAGACAACGGACCCGCCGACCAACGTCCC<br>1261<br>1350<br>ATTCATGACCGGGACGACGTGTTGTGTTACAGCACTGAGGTATTGACCGACCCGGTGGAAGTAACCGGCACCGTCTCCGCCCGGCTGTTC |

| SEQUENCES |
|---|
| 1351                                                                      1440<br>GTGTCGTCATCAGCGGTGGACACTGATTTCACCGCCAAACTTGTCGACGTATTTCCCGACGGTCGCGCGATCGCGCTGTGTGACGGGATC<br>1441                                                                      1530<br>GTGCGGATGCGGTACCGCGAGACGTTGGTCAATCCAACCTTGATCGAAGCGGGCGAAATCTACGAGGTTGCTATCGACATGCTTGCAACC<br>1531                                                                      1620<br>TCGAATGTATTCCTGCCAGGGCATCGCATCATGGTCCAAGTATCAAGTAGCAACTTCCCGAAATACGACCGCAATTCGAATACCGGCGGA<br>1621                                                                      1710<br>GTAATCGCACGGGAACAGCTCGAAGAGATGTGCACCGCCGTGAACCGCATTCACCGAGGACCTGAGCATCCCAGCCACATTGTGCTGCCG<br>1711<br>ATTATCAAGCGA<br><br>SEQ ID NO: 4<br>T172R/G173Q/L196C/I301C CocE<br>1                                                                                     60<br>MVDGNYSVASNVMVPMRDGVRLAVDLYRPDADGPVPVLLVRNPYDKFDVFAWSTQSTNWL<br>61                                                                                    120<br>EFVRDGYAVVIQDTRGLFASEGEFVPHVDDEADAEDTLSWILEQAWCDGNVGMFGVSYLG<br>121                                                                                   180<br>VTQWQAAVSGVGGLKAIAPSMASADLYRAPWYGPGGALSVEALLGWSALIG<u>RQ</u>LITSRSD<br>181                                                                                   240<br>ARPEDAADFVQLAAI<u>C</u>NDVAGAASVTPLAEQPLLGRLIPWVIDQVVDHPDNDESWQSISL<br>241                                                                                   300<br>FERLGGLATPALITAGWYDGFVGESLRTFVAVKDNADARLVVGPWSHSNLTGRNADRKFG<br>301                                                                                   360<br><u>C</u>AATYPIQEATTMHKAFFDRHLRGETDALAGVPKVRLFVMGIDEWRDETDWPLPDTAYTP<br>361                                                                                   420<br>FYLGGSGAANTSTGGGTLSTSISGTESADTYLYDPADPVPSLGGTLLFHNGDNGPADQRP<br>421                                                                                   480<br>IHDRDDVLCYSTEVLTDPVEVTGTVSARLFVSSSAVDTDFTAKLVDVFPDGRAIALCDGI<br>481                                                                                   540<br>VRMRYRETLVNPTLIEAGEIYEVAIDMLATSNVFLPGHRIMVQVSSSNFPKYDRNSNTGG<br>541<br>VIAREQLEEMCTAVNRIHRGPEHPSHIVLPIIKR<br>Note: Residues labeled in red are: R172, Q173, C196, and C301 |

We claim:

1. A cDNA molecule comprising the sequence of SEQ ID NO: 3.

2. A cDNA molecule comprising a nucleic acid sequence which encodes a cocaine esterase (CocE) polypeptide variant, comprising the amino acid sequence of SEQ ID NO: 4.

3. A cocaine esterase (CocE) polypeptide variant, comprising the amino acid sequence of SEQ ID NO: 2, including the amino acid sequences mutations: T172R, G173Q, L196C, and I301C.

4. A cocaine esterase (CocE) polypeptide variant, comprising the amino acid sequence of SEQ ID NO: 4, or the amino acid sequence encoded by the nucleic acid sequence of SEQ ID NO: 3.

5. The CocE polypeptide variant of claim 4, comprising at least one cross-subunit disulfide bond.

6. The CocE polypeptide variant of claim 4, wherein the at least one cross-subunit disulfide bond is a bond between C196a and C301b, or C301a and C196b.

7. The CocE polypeptide variant of claim 4, having a half-life of greater than about 100 days at 37° C.

8. The CocE polypeptide variant of claim 4, further comprising at least one polyethylene glycol polymer chain attached thereto.

9. The CocE polypeptide variant of claim 5, wherein the enzyme is conjugated to the polyethylene glycol polymer and the polyethylene glycol polymer maleimide-linked branched poly(ethylene glycol) (PEG).

10. A pharmaceutical composition comprising the CocE polypeptide variant of claim 4; and a suitable pharmaceutically carrier.

11. The pharmaceutical composition comprising of claim 10, and further comprising at least one polyethylene glycol polymer chain attached thereto.

12. A method of treating a cocaine-induced condition comprising administering to an individual an effective amount of the CocE polypeptide variant of claim 4 to accelerate cocaine metabolism and produce biologically inactive metabolites.

13. The method of claim 12, wherein said CocE polypeptide variant exhibits a one-hundred-fold or more increase in cocaine hydrolysis catalytic efficiency as compared to a mutant that includes only the T172R/G173Q mutations.

14. The method of claim 12, wherein said CocE polypeptide variant provides protection from a lethal dose of cocaine for at least 72 hours.

* * * * *